United States Patent [19] [11] 4,065,554
Tilly et al. [45] Dec. 27, 1977

[54] X-RAY CONTRAST MEDIA

[75] Inventors: Guy Tilly; Michel Jean Charles Hardouin; Jean Lautrou, all of Aulnay-sous-Bois, France

[73] Assignee: Laboratoires Andre Guerbet, Aulnay-sous-Bois, France

[21] Appl. No.: 747,810

[22] Filed: Dec. 6, 1976

Related U.S. Application Data

[62] Division of Ser. No. 579,279, May 20, 1975, Pat. No. 4,014,986.

[30] Foreign Application Priority Data

May 31, 1974 United Kingdom ............... 24169/74
July 31, 1974 United Kingdom ............... 33900/74

[51] Int. Cl.[2] ...................... A61K 29/02; C07C 103/84
[52] U.S. Cl. .................................. 424/5; 260/501.11; 260/518 A; 260/519; 560/37; 560/42; 560/251

[58] Field of Search ............... 260/471 R, 518 A, 519, 260/501.11, 490; 424/5

[56] References Cited

U.S. PATENT DOCUMENTS

| | | | |
|---|---|---|---|
| 3,178,473 | 4/1965 | Holtermann et al. | 260/519 |
| 3,541,141 | 11/1970 | Bernstein et al. | 260/518 A |
| 3,660,464 | 5/1972 | Bernstein et al. | 424/5 X |
| 3,939,204 | 2/1976 | Buttermann | 260/518 A |

*Primary Examiner*—Richard L. Raymond
*Attorney, Agent, or Firm*—Young & Thompson

[57] ABSTRACT

The present invention provides new iodo benzene derivatives which have at least two benzene nuclei and one carboxylic group.

These derivatives possess a low toxicity and may be used as X-ray contrast media.

4 Claims, No Drawings

X-RAY CONTRAST MEDIA

This is a division of application Ser. No. 579,279, filed May 20, 1975 now U.S. Pat. No. 4,014,986.

This invention relates to new polyiodo benzene derivatives useful as X-ray contrast media.

The present invention relates, more particularly, to new compounds comprising at least two benzene nuclei and a single carboxyl group which have low toxicity, provide good contrast, which may be prepared according to industrially useful methods and which, therefore, are of relatively low cost.

The formula of a compound comprising two tri-iodo benzene nuclei and a single carboxyl group as already been given in U.S. Pat. No. 2,708,678. This formula is as follows:

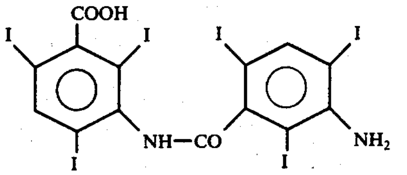

However, the attempts made by Applicant to prepare this compound according to the process described in said patent were all unsuccessful, whatever the operating conditions used.

The present invention relates to compounds of the formula (I)

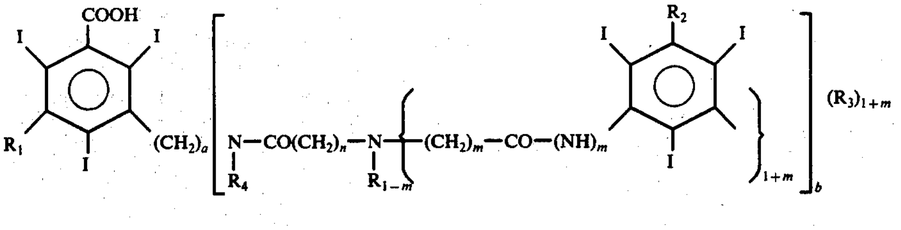

in which:

$R_1$ represents a hydrogen atom, a radical of the formula

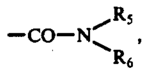

$R_5$ and $R_6$ being a hydrogen atom, a lower alkyl radical, a lower hydroxyalkyl radical or a lower alkanoyloxyalkyl radical, or a radical of the formula

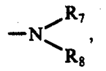

$R_7$ being a lower alkanoyl radical and $R_8$ being a hydrogen atom, a lower alkyl radical, a lower hydroxyalkyl radical or a lower alkanoyl radical, $R_2$ represents a hydrogen atom, a radical of the formula

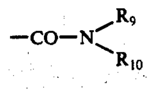

in which $R_9$ and $R_{10}$ have the meanings given for $R_4$ and $R_5$, or a radical of the formula

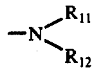

in which $R_{11}$ has the meaning given for $R_7$ or represents a hydrogen atom and $R_{12}$ has the meaning given for $R_8$, $r_3$ represents a hydrogen atom, a radical of the formula

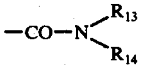

in which $R_{13}$ and $R_{14}$ have the meanings given for $R_5$ and $R_6$, or a radical of the formula

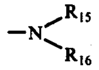

in which $R_{15}$ has the meaning given for $R_7$ or represents a hydrogen atom or a polyhydroxy lower alkanoyl radical and $R_{16}$ has the meaning given for $R_8$, $R_4$ represents a hydrogen atom, a lower alkyl radical or a lower hydroxyalkyl radical,

*a* is 0 or 1

*n* is an integer from 1 to 5

*m* is 0 or 1

*b* is 1 or 2, the sum *b* + *m* being 2 or less, and their lower alkyl esters and their salts with pharmaceutically acceptable bases.

By lower alkyl and hydroxyalkyl radicals are essentially meant radicals having 1–4 carbon atoms and by lower alkanoyl and hydroxy lower alkanoyl radicals are essentially meant radicals having 2–6 carbon atoms.

As salts of acids of the formula (I) may be mentioned, in particular, alkali metal (such as sodium and potassium) salts, the ammonium salts, the alkaline-earth (such as calcium) salts and the organic base salts (e.g. such as ethanolamine or methylglucamine salts).

The compounds according to the present invention may be prepared by reacting an amine of the formula:

(IV)

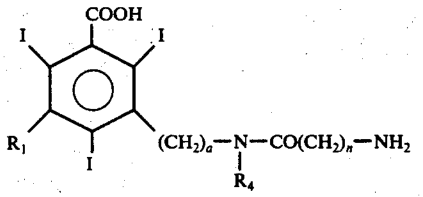

with a chlorinated compound of the formula:

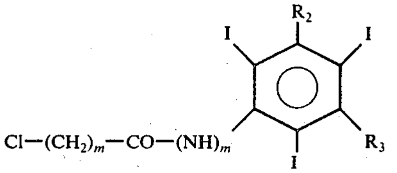
(V)

$R_1$, $R_2$, $R_3$, $R_4$, *a*, *m* and *n* having the aforesaid meanings.

If desired, this reaction may be followed by a N-alkylation, N-hydroxyalkylation, N-acylation or N-polyhydroxyacylation reaction, by a deacylation reaction, and also by esterification of salt-forming reactions, according to conventional methods.

Amines of the formula (IV) (in which $a = 0$, $n = 1$, $R_4 = H$ and $R_1 = H$, $-CONHCH_3$ and $-NHCOCH_3$) are described in U.S. Pat. No. 3,210,412.

The amines of the formula (IV) in which $R_4$ is hydrogen may be prepared by condensation of an amine of the formula:

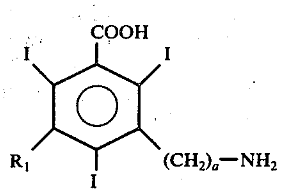
(VI)

with an acid chloride having the formula:

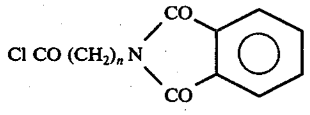
(VII)

acid chloride being used in an excess amount. Reaction time may vary from 2 hours to about 4 days.

The hydrazinolysis reaction of the product of the formula (VIII) is carried out according to usual techniques, by action of hydrazine in aqueous medium (see, in this respect, J. Am. Chem. Soc., 71, 1856 (1949); H. R. Ing and R. F. Manske, J. Chem. Soc., 2348 (1926); Chem. Ber. 83 244 (1950)). A large excess of hydrazine is advantageously used (4–8 moles per mole of product of the formula (VIII)).

The amines of the formula (IV) in which $n = 1$ and $a = 0$ and $R_4$ is a lower alkyl radical may also be prepared by reacting a compound having the formula:

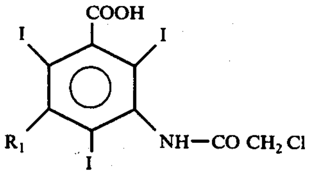
(IX)

with an alkylating agent, to give a compound of the formula:

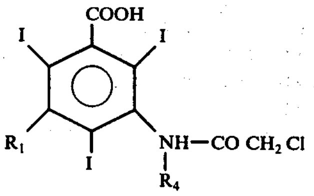
(X)

in which $R_4$ is a lower alkyl radical, with subsequent reaction of ammonia with the resulting compound.

A preferred class of compounds of the formula (I) is represented by the compounds having the formula:

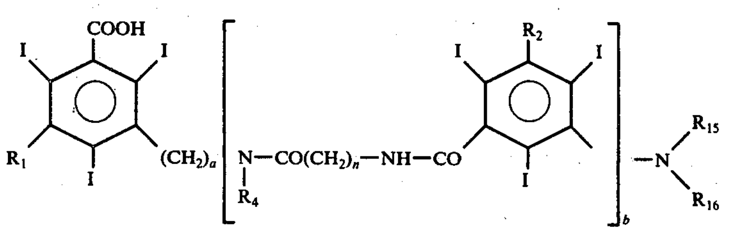
(II)

$R_1$, *a* and *n* having the aforesaid meanings, with subsequent hydrazinolysis of the resulting condensation product of the formula:

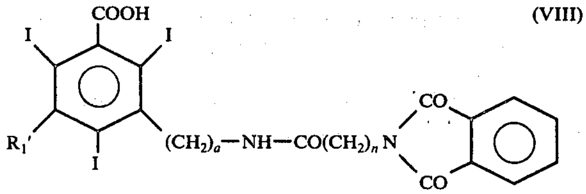
(VIII)

in which *a* and *n* have the aforesaid meanings and $R'_1$ has the same meaning as $R_1$ or, in the case where $R_1$ comprises a hydroxy group, $R'_1$ represents its acylation product with acid chloride of the formula (VII).

The condensation reaction of the amine of the formula (IV) with acid chloride (VII) is advantageously effected in a polar solvent such as dimethylacetamide or dimethylformamide, at a temperature of 20°–100° C, the in which:

$R_1$ represents a hydrogen atom, a radical having the formula

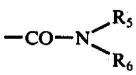
, $R_5$ and $R_6$ being each a hydrogen atom, a lower alkyl radical, a lower hydroxyalkyl radical or a lower alkanoyloxyalkyl radical, or a radical of the formula

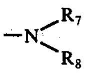
, $R_7$ being a lower alkanoyl radical and $R_8$ being a hydrogen atom, a lower alkyl or lower hydroxyalkyl radical, $R_2$ represents a hydrogen atom, a radical having the formula

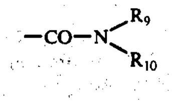

in which $R_9$ and $R_{10}$ have the meanings given for $R_5$ and $R_6$, or a radical of the formula

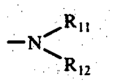

in which $R_{11}$ has the meaning given for $R_7$ or represents a hydrogen atom and $R_{12}$ has the meaning given for $R_8$, $R_4$ represents a hydrogen atom, a lower alkyl radical or a lower hydroxyalkyl radical, $R_{15}$ represents a hydrogen atom, a lower alkanoyl radical or a polyhydroxy lower alkanoyl radical, $R_{16}$ represents a hydrogen atom, a lower alkyl radical, a lower hydroxyalkyl radical or a lower alkanoyl radical,

*a* is 0 or 1

*n* is an integer from 1 to 5

*b* is 1 or 2 and the different $R_2$, $R_4$ and *n* which exist when $b = 2$ may have the same or different meanings, and their lower alkyl esters and their salts with pharmaceutically acceptable bases.

Said compounds of the formula (II) may be prepared by condensing an amine of the formula (IV) as previously defined with an acid chloride having the formula:

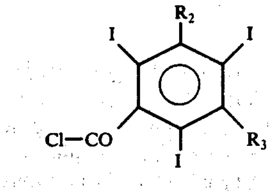

(Va)

This condensation reaction is advantageously effected within a polar solvent such as dimethylacetamide,dimethylsulfoxide,dimethylformamide or a mixture water-dioxane, at a temperature of 20°-60° C, in the presence of an acil binding agent such as triethylamine or sodium carbonate in excess amount. Reaction time may vary from 2 hrs to about 4 days.

To obtain a compound of the formula (II) in which $R_4$ is an alkyl or hydroxyalkyl radical, a compound of the formula (II) in which $R_4$ is hydrogen may be reacted with an alkylating or hydroxyalkylating agent, according to conventional methods.

To obtain a compound of the formula (II) in which $R_{15}$ is a lower alkanoyl radical or a polyhydroxy lower alkanoyl radical, a compound of the formula (II) in which $R_{15}$ and $R_{16}$ are hydrogen atoms may be reacted with an acylating or polyhydroxyacylating agent, according to conventional methods.

Conversely, a compound of the formula (II) in which $R_{15}$ and $R_{16}$ are hydrogen atoms may be obtained by saponification (deacylation) of N-acylated compounds of the formula (II).

The compounds of the formula (II) in which $b = 2$, may be prepared using as amine of the formula (VI) a compound of the formula (II) in which $R_{15}$ and $R_{16}$ are hydrogen atoms.

Another preferred class of compounds of the formula (I) is represented by the compounds having the formula:

(III)

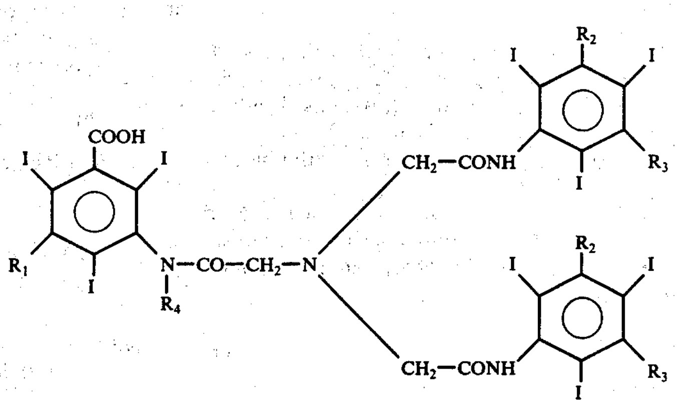

in which:

$R_1$ represents a hydrogen atom, a radical having the formula

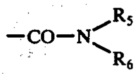

in which $R_5$ and $R_6$ are a hydrogen atom, a lower alkyl radical or a lower hydroxy alkyl radical or a radical of the formula

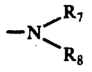

in which $R_7$ is a lower alkanoyl radical and $R_8$ is a hydrogen atom, a lower alkyl radical or a lower hydroxyalkyl radical, $R_2$ represents a hydrogen atom, a radical having the formula

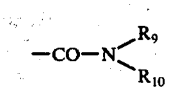

in which $R_9$ and $R_{10}$ have the meanings given for $R_4$ and $R_5$, or a radical of the formula

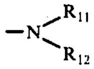

in which $R_{11}$ has the meaning given for $R_7$ or represents a hydrogen atom and $R_{12}$ has the meaning given for $R_8$, $R_3$ represents a hydrogen atom, a radical having the formula

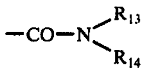

in which $R_{13}$ and $R_{14}$ have the meanings given for $R_5$ and $R_6$, or a radical of the formula

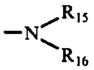

in which $R_{15}$ has the meaning given for $R_7$ or represents a hydrogen atom and $R_{16}$ has the meaning given for $R_8$, $R_4$ represents a hydrogen atom, a lower alkyl radical or a lower hydroxyalkyl radical, and their lower alkyl esters and their salts with pharmaceutically acceptable bases.

Said compounds of the formula (III) may be prepared by reacting an amine of the formula (IV) as previously defined (in which $a = 0$) with a chlorinated compound of the formula:

(Vb)

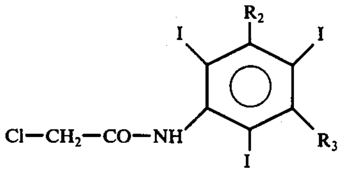

This reaction is advantageously effected in basic aqueous medium, for example in excess normal sodium hydroxide, at a temperature of 60°-90° C. The reaction time may vary from 6 to 48 hours.

The chlorinated compounds of the formula (Vb) may be prepared by reaction of chloroacetyl chloride with the corresponding aniline, under conventional conditions, followed, if desired, by a saponification.

The following examples are given to illustrate the invention. The preparation of amines of the formula (IV), of derivatives of the formula (V) and of compounds of the formula (I) is described in following sections A, B and C, respectively.

In said examples, purity controls were effected by:

1. Thin-layered chromatography (TLC) over fluorescent Silicagel plate (Merck F 254 grade) in the following eluents:
   1 — Benzene/methylethyl ketone/formic acid (60:25:20) Eluent 1.
   2 — Ethyl acetate/isopropanol/ammonia (55:35:40) Eluent 2.
   3 — Ethyl acetate/isopropanol/ammonia (35:35:40) Eluent 3.
   4 — n-Butanol/acetic acid/water (50:11:25) Eluent 4.

Note: With certain TLC eluents (particularly eluent 4), it is possible to evidence the different isomers of acids containing a N-methyl N-acylamino benzoic function.

Thus, a pure mono-N-methyl compound of the formula (I) will give 2 spots (slightly spaced apart, but clearly distinct, and in varying ratios according to the acids), and a di-N-methyl compound will give 3 spots.

2. Purity determination according to:
   1 — Halogen titration
   2 — Carboxylic acid titration : back-titration with sodium hydroxide.
   3 — Labile hydrogen and carboxylic acid titration with sodium methoxide in non-aqueous medium, in the presence of azoviolet.
   4 — Titration of carboxylic acid in dimethylformamide solution, by means of tetrabutylammonium hydroxide in isopropanol solution.
   5 — Titration of aliphatic amines, by means of perchloric acid in acetic medium.

A. PREPARATION OF AMINES OF THE FORMULA (IV)

I. Preparation of 2,4,6-triiodo-3-N-hydroxyethylcarbamyl-5-aminoacetylamino-benzoic acid (Compound I)

a. Preparation of 2,4,6-triiodo-3-N-phthalimido-acetoxyethylcarbamyl-5-phthalimidoacetylamino-benzoic acid

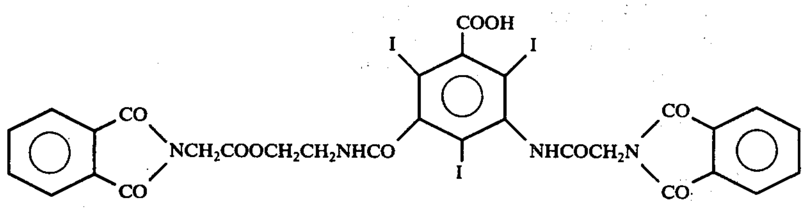

2,4,6-Triiodo-3-N-hydroxyethylcarbamyl-5-amino-benzoic acid (180 g; 0.3 mole) is dissolved in dimethylacetamide (300 ml). Phthalylglycine acid chloride (170 g; 0.76 mole) is added portionwise (while cooling over an ice bath). After stirring overnight at room temperature, the reaction mixture is diluted with water (1000 ml). Precipitation occurs. The resulting material is suction filtered, washed repeatedly with water, suction filtered and oven-dried, to give 275 of white material. Yield: 95%.

Purity control:

TLC eluent 1.

Rf of the starting triiodo acid: 0.4

Rf of the starting phthalylglycine: 0.77

Rf of the condensation product: 0.68 b. Preparation of 2,4,6-triiodo-3-N-hydroxyethyl-carbamyl-5-aminoacetamido-benzoic acid

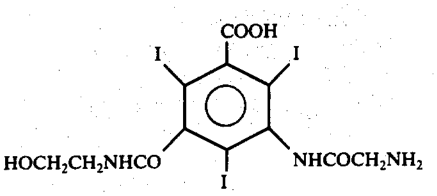

The preceding product (197 g; 0.20 mole) is suspended in water (600 ml) and hydrazine hydrate (60 g) and heated at 80° c during 2 hours, with stirring (dissolution occurs). Crystallization occurs during the reaction. After cooling, suction filtering, washing and oven-drying, there are obtained 125 g of product. Yield: 95%.

Purity control:

1. TLC eluent 1
   Rf of the starting material: 0.68
   Rf of the product obtained: 0.05

An orange-yellow spot is obtained on development with ninhydrin.

2. Purity of the product according to the iodine titration: 97.7%
3. Purity of the product according to titration with sodium hydroxide: 100%

II. Preparation of 2,4,6-triiodo-3-N-methylcarbamyl-5-γ-aminobutyrylamino-benzoic acid (Compound II)

The same procedure is used as for Compound I, using 2,4,6-triiodo-3-N-methyl-carbamyl-5-amino-benzoic acid as iodo starting material and γ-phthalimidobutyric acid chloride as acid chloride.

III. Preparation of 2,4,6-triiodo-3-N-methyl-carbamyl-5-aminoacetylamino-benzoic acid (Compound III)

the same procedure is used as for Compound I, using 2,4,6-triiodo-3-N-methyl-carbamyl-5-aminobenzoic acid as starting material.

In addition, the crude product is purified: it is taken up into 95% ethanol (about 3000 g/5 liters). The mixture is heated to refluxing temperature and is then filtered hot. Overall yield condensation + purification = 62.5%.

IV. Preparation of 2,4,6-triiodo-3-acetamido-5-aminoacetamidomethyl-benzoic acid (Compound IV)

The same procedure is used as for Compound I, using 2,4,6-triiodo-3-acetamido-5-aminomethyl-benzoic acid as starting material, obtained under the following conditions:

2,4,6-Triiodo-2,4,6-acetamido-5-acetamidomethyl-benzoic acid (111 g; 0.177 mole) (Swiss Pat. No. 13,788/62) is dissolved in 10N sodium hydroxide (220 ml). The resulting solution is heated 2 hours at 70° C, after which it is cooled to 0° C and adjusted at pH 7 with concentrated hydrochloric acid. It is then left to crystallize overnight in the refrigerator and is then suction filtered, washed repeatedly with water, suction filtered and oven-dried, to give 100 g of product. Yield: 96%.

Purity control:

1. TLC eluent 1
   Rf of the starting material: 0.30
   Rf of the product obtained: 0.25
2. Purity of the product according to the iodine titration: 99.5%

Condensation of 2,4,6-triiodo-3-acetamido-5-aminomethyl-benzoic acid and phthalylglycine chloride. The triiodo acid (100 g; 0.17 mole) is dissolved in DMAC (200 ml). Phthalylglycine acid chloride (55 g; 0.25 mole) is added thereto and the mixture is allowed to react overnight at room temperature. A further amount of phthalylglycine acid chloride (20 g) is added after 24 hours, and, 24 hours later, a further amount (45 g) of phthalylglycine acid chloride is added.

Precipitation of the product, washing, suction filtering, drying and subsequent hydrazinolysis are then carried out as described for Compound I.

V. Preparation of 2,4,6-triiodo-3-ε-aminocaproylamino-benzoic acid (Compound V)

The same procedure is used as for Compound I, using 2,4,6-triiodo-3-amino-benzoic acid as iodo starting material and ε-phthalimidocaproic acid chloride.

VI. Preparation of 2,4,6-triiodo-3-aminoacetamido-benzoic acid (Compound VI)

The same procedure is used as for Compound I, using 2,4,6-triiodo-3-amino-benzoic acid as iodo starting material.

VII. Preparation of 2,4,6-triiodo-3-acetamido-5-aminoacetamido-benzoic acid (Compound VII)

The same procedure is used as for Compound I, using 2,4,6-3-acetamido-5-amino-benzoic acid as iodo starting material. VIII. Preparation of 2,4,6-triiodo-3-N-methyl-carbamyl-5-N-methyl-N-aminoacetylamino-benzoic acid (Compound VIII)

a. 2,4,6-Triiodo-3-N-methyl-carbamyl-5-N-methyl-chloroacetamido-benzoic acid:

Dimethyl sulfate (380 ml; 4 moles) is added dropwise, at 5°-10° C, to a solution of 2,4,6-triiodo-3-N-methyl-carbamyl-5-chloroacetamido-benzoic acid (1300 g; 2 moles) (U.S. Pat. No. 3,210,412) in a 2N sodium hydroxide solution (2 liters). When addition is complete, the reaction mixture is allowed to warm to room temperature and stirring is continued a further 20 hours. The reaction mixture is then filtered, a slight insoluble is removed, and the material is made acidic to pH 1 with concentrated hydrochloric acid. The resulting precipitate is suction filtered, washed repeatedly with water and dried at 60° C. Purification is carried out by dissolving the crude material in 900 ml 2N sodium hydroxide and salting out with sodium chloride (1000 g). After stirring 24 hours at room temperature, the precipitate is suction filtered and redissolved in water (2500 ml). After which it is filtered and made acidic to pH 1 with concentrated hydrochloric acid. It is then repeatedly washed with water, suction filtered, dried at 60° C, to give 672 g of product (Yield: 51%).

Purity control:

1. TLC eluent 2
   Rf of starting material: 0.1
   Rf of the methyl product: 0.2 and 0.25 (2 isomers)

2. Purity: iodine titration: 97%, chlorine titration 104% b.
2,4,6-triiodo-3-N-methyl-carbamyl-5-N-methyl-N-aminoacetyl-amino-benzoic acid:

The preceding acid (314 g; 0.49 mole) is dissolved in 3500 ml concentrated ammonia and heated 20 hours at 60° C. After evaporation to dryness, in vacuo, the material is taken up into 300 ml water and made acidic with sulfur dioxide. It is then left to crystallize in the refrigerator during 48 hours, suction filtered, washed repeatedly with water and dried in an oven at 80° C, to give 160 g (Yield: 51%) of product.

Purity control:
1. TLC eluent 3
   Rf of the product obtained: 0.75
2. Purity: titration with sodium hydroxide: 102%
   Purity: titration with sodium methoxide: 98%

IX. Preparation of
2,4,6-triiodo-3-N-methylcarbamyl-5-(2,4,6-triiodo-3-N-methyl-N-acetylamino-5-aminoacetylamino-benzoyl)-glycylamino-benzoic acid (Compound IX)

The same procedure is used as for Compound I, using 2,4,6-triiodo-3-N-methylcarbamyl-5-(2,4,6-triiodo-3-N-methyl-N-acetylamino-5-amino-benzoyl)-glycylamino-benzoic acid (Compound 15 described hereinafter) as iodo starting material, the sole exception being a longer reaction time (4 days at room temperature).

X. Preparation of
2,4,6-triiodo-3-N-methyl-N-aminoacetylamino-benzoic acid (Compound X)

a. Preparation of
2,4,6-triiodo-3-chloroacetamido-benzoic acid
(according to U.S. Pat. No. 3,210,412).

Purity control:
1. TLC eluent 2
   Rf of starting material: 0.3
   Rf of the product obtained: 0.25
2. Purity: titration with sodium hydroxide: 99.8% b.
2,4,6-Triiodo-3-N-methyl-N-chloroacetylamino-benzoic acid

The above product (591.5 g; 1 mole) is dissolved in 5N sodium hydroxide (2.3 moles) and acetone (100 ml).

Methyl iodide (1.3 mole) is added dropwise, while maintaining the temperature at 10° C by means of an ice-bath. After stirring during 16 hours at room temperature, the reaction mixture is poured over 2 liters dilute (1/10) hydrochloric acid, while cooling by means of an ice-bath. The resulting precipitate is suction filtered, washed repeatedly with water and dried in an oven at 50° C, to give 591 g (Yield: 85%) of product.

Purity control:
1. TLC eluent 2
   Rf of starting material: 0.25
   Rf of the methyl product (separation of 2 isomers): 0.35 and 0.45
2. Purity: chlorine titration: 92%
   iodine titration: 100%
   Purity: titration with sodium methoxide: 92% c.
2,4,6-Triiodo-3-N-methyl-N-aminoacetylaminobenzoic acid:

The preceding acid (590 g; 0.90 mole) is dissolved in 9 liters concentrated ammonia. Dissolution is substantially complete (filtration remove 3 g of insoluble matter which is the methyl ester of the starting acid).

The resulting solution (pale yellow) is heated during 20 hours at 60° C and then concentrated to 2 liters, in vacuo. The ammonium salt crystallizes; it is suction filtered and redissolved in water (500 ml) and the minimum volume of sodium hydroxide, after which it is reprecipitated at pH 4 with acetic acid, to give, after suction filtering, repeated washing with water, suction filtering and drying 316 g of white product (Yield: 52%).

Purity control:
1. TLC eluent 1
   Rf of starting material: 0.9
   Rf of the product obtained: 0.25 (yellow spot on development with ninhydrin).
2. Purity: titration with sodium hydroxide: 98.5%
   Purity: titration with sodium methoxide: 100%.

XI. Preparation of
2,4,6-triiodo-3-N-γ-aminobutyrylamino-benzoic acid (Compound XI)

The same procedure is used as for Compound II, using 2,4,6-triiodo-3-amino-benzoic acid as iodo starting material.

In this case, it is necessary to purify the resulting crude product by dissolution of 350 g in 4 liters water and 280 ml concentrated sulfuric acid.

The insoluble impurities are filtered off, the solution is neutralized and the amino is then reprecipitated with acetic acid at pH 4, to give 309 g of purified product.

XII. Preparation of
2,4,6-triiodo-3-β-aminopropionylaminobenzoic acid (Compound XII)

The same procedure is used as for Compound I, using 2,4,6-triiodo-3-amino-benzoic acid as iodo starting material and β-phthalimidopropionic acid chloride.

XIII. Preparation of
2,4,6-triiodo-3-N-methyl-N-acetylamino-5-amino-acetamido-benzoic acid (Compound XIII)

The same procedure is used as for Compound I, using 2,4,6-triiodo-3-N-methyl-N-acetylamino-5-amino-benzoic acid (U.S. Pat. No. 3,178,473) except that:
1. The condensation product with phthalylglycine is washed (1554 g of product in 2 liters 95% ethyl alcohol, to give 1200 g purified product).
2. The crude hydrazinolysis product is purified by dissolving 267 g in 550 ml dilute sulfuric acid (1/10) at 80° C.

It is filtered hot and 25 g phthalhydrazide are removed:

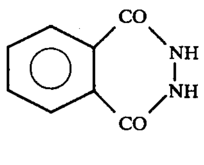

The sulfruic filtrate is treated with charcoal and neutralized to pH 4–5 with ammonia. It is then crystallized, repeatedly washed with water, suction filtered and dried in an oven at 70° C, and then at 105° C, to give 211 g of white material.

3. 390 g of white material of same grade as the preceding 211 g are recovered by treating the hydrazinolysis liquid with sulfuric acid in the hot.

XIV. Preparation of 2,4,6-triiodo-3-N-hydroxyethyl-carbamyl-5-amino-butyrylamino-benzoic acid (Compound XIV)

The same procedure is used as for Compound II, using 2,4,6-triiodo-3-hydroxyethyl-carbamyl-5-amino-benzoic acid as iodo starting material.

XV. Preparation of 2,4,6-triiodo-3-N-methyl-carbamyl-5-(2,4,6-triiodo-3-N-methylcarbamyl-5-aminoacetamido-benzoyl)-glycyl-N-methylamino-benzoic acid (Compound XV)

The same procedure is used as for Compound I, using compound 14*a*, described hereinafter, as iodo starting material.

XVI. Preparation of 2,4,6-triiodo-5-(2,4,6-triiodo-3-N-methylcarbamyl-5-aminoacetamido-benzoyl)-glycyl-amino-benzoic acid (Compound XVI)

The same procedure is used as for Compound I, using compound 34, described hereinafter, as iodo starting material.

XVII. Preparation of 2,4,6-triiodo-3-N-hydroxyethyl-carbamyl-5-(2,4,6-triiodo-3-N-methylcarbamyl-5-aminoacetamido-benzoyl)-glycly-amino-benzoic acid (Compound XVII)

The same procedure is used as for Compound I, using compound 3*a*, described hereinafter, as starting material.

XVIII. Preparation of 2,4,6-triiodo-3-N-methyl-carbamyl-5-amino-propionylamino-benzoic acid (Compound XVIII)

The same procedure is used as for Compound I, using 2,4,6-triiodo-3-N-methylcarbamyl-5-amino-benzoic acid as starting material.

In Table I are set forth data relating to the preparation of amines of the formula (IV) by condensation and hydrazinolysis and to the resulting amines. In Table II are set forth data relating to the preparation of amines of the formula (IV) from chlorinated derivatives of the formula (IX) and to the resulting amines.

In Table III, are illustrated the structural formulae of the amines of general formula (IV) thus prepared.

In following Table I:

1. after washing with DMF in the hot
2. in benzene/methylethylketone/formic acid (80:20:10) eluent.

TABLE I

| | Triiodo starting material | Condensation product | | Amines obtained by hydrazinolysis | | |
|---|---|---|---|---|---|---|
| Amine | Rf in eluent 1 | Rf in eluent 1 | Yield | Rf in eluent 1 | Rf in eluent 2 | Yield |
| I | 0.4 | 0.68 | 95% | 0.05 | 0.5 | 95% |
| II | 0.7 | 0.5 | 100% | 0.05 | 0.15 eluent 4 | 95% |
| III | 0.65 | 0.4 | 100% | 0.05 0.1 | 0.45 | 62% |
| IV | 0.1 | 0.45 | 89% | 0.05 | 0.5 | 85% |
| V | 0.9 | 0.75 | 100% | 0.15 | | 87% |
| VI | 0.7 | 0.55 (2) | uniso-lated | 0.5 | 0.1 eluent 3 | 71% (overall yield) |
| VII | 0.5 | 0.4 | 85% | 0.05 | 0.44 | 73% |
| IX | 0.4 | 0.3 | 83% | 0.05 | 0.55/0.60 | 83% |
| XI | 0.9 | 0.80 | 100% | 0.2 | 0.05 | 81% |
| XII | 0.9 | 0.85 | 100% | 0.2 | 0.2 0.1 in eluent 4 | 75% |
| XIII | 0.65 | 0.4 | 90% | 0.05 | 0.45 0.53 | 66% |
| XIV | 0.4 | 0.6 | uniso-lated | 0.0 | 0.1 | 58% (overall yield) |
| XV | 0.4 | 0.35 | 72% | 0.0 | 0.25 | 50% |
| XVI | 0.4 | 0.3 | 92% | 0.05 | 0.1 in eluent 3 | 41% |
| XVII | 0.15 | 0.3 | 97% | 0.0 | 0.5 | 50% (1) |
| XVIII | 0.7 | 0.45 | 85% | 0.05 | 0.02 | 53% |

TABLE II

| | Triiodo starting material | Chlorinated condensation product | | | Amine | | |
|---|---|---|---|---|---|---|---|
| Amine | Rf in eluent 2 | Rf in eluent 2 | Rf in eluent 1 | Yield | Rf in eluent 1 | Rf in eluent 2 | Yield |
| VIII | 0.1 | 0.2 and 0.25 | 0.5 | 51% | 0.3 in eluent 4 | 0.75 | 51% |
| X | 0.25 | 0.3 and 0.25 | 0.9 | 97% | 0.25 | 0.15 and 0.25 | 54% |

TABLE III

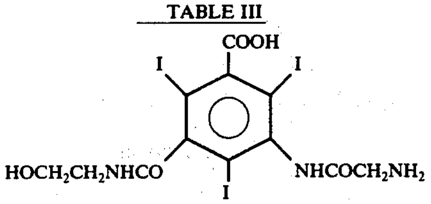

I

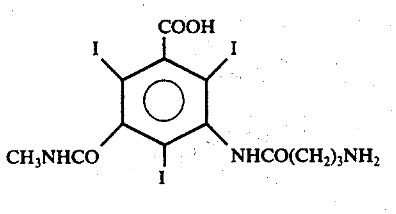

II

-continued
III
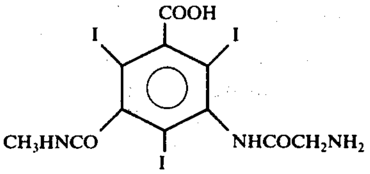
IV
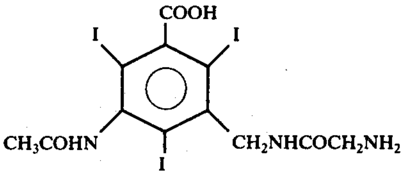
V
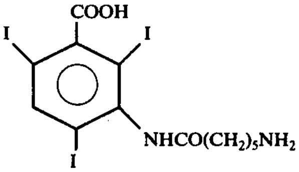
VI
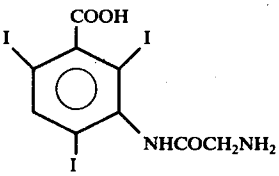
VII
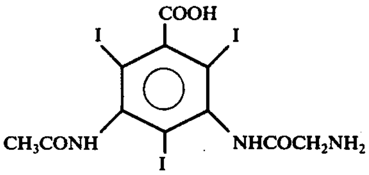
VIII
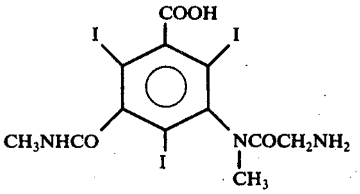
IX
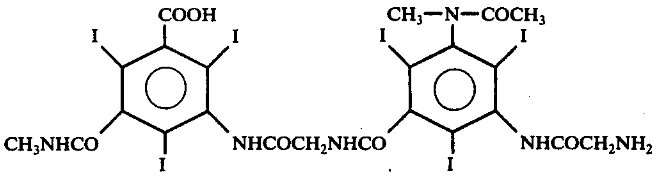
X
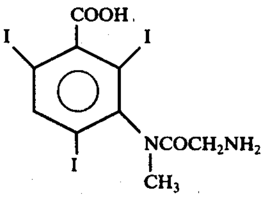
XI
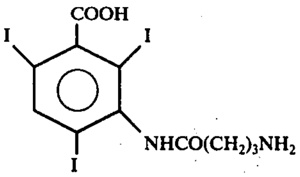

-continued

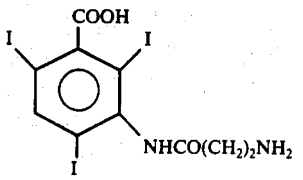

XII

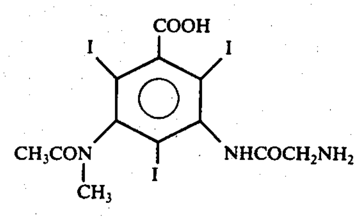

XIII

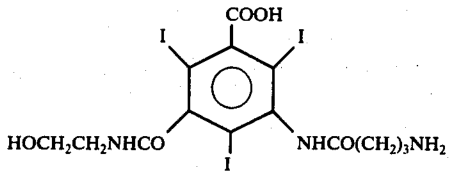

XIV

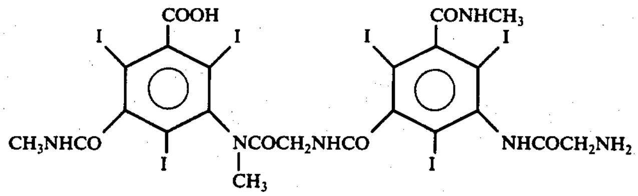

XV

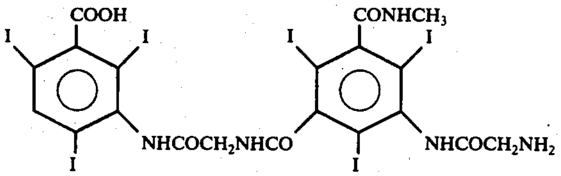

XVI

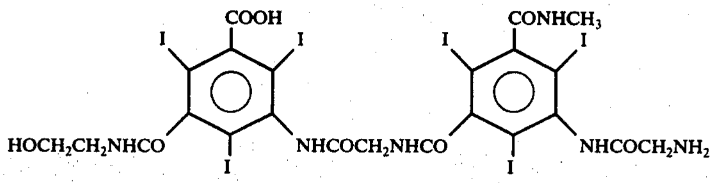

XVII

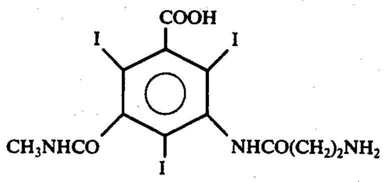

XVIII

B. PREPARATION OF DERIVATIVES OF THE FORMULA (V)

XIX. Preparation of 2,4,6-triiodo-3-N-methylcarbamyl-5-N-acetyl-N-methylamino-benzoic acid chloride (Compound XIX 2,4,6-Triiodo-3-methylcarbamyl-5-N-acetyl-N-methylaminobenzoic acid (50 g) (described in French Pat. No. 2,085,636) is suspended in thionyl chloride (90 ml). The suspension is heated at 65° C during 5 hours, with stirring. The resulting slurry is allowed to cool. The acid chloride is suction filtered and washed with diisopropyl ether; it is then dried in vacuo, to give 37 g of product (Yield: 73%).

Purity control:

TLC after reaction with excess propylamine in dimethylacetamide: Eluent 1.

Rf starting material: 0.5

Rf of propylamine condensate: 0.83

XX. Preparation of 2,4,6-triiodo-3-methylcarbamyl-5-amino-benzoic acid chloride (Compound XX)

The same procedure is used as for compound XIX, using 2,4,6-triiodo-3-N-methylcarbamyl-5-amine-benzoic acid as starting material (Yield: 85%).

Purity control:

1. TLC: same technique as with the preceding product, but after condensation with ethanolamine
   Rf of starting acid: 0.8

Rf of condensate: 0.4

2. TLC in acetone/chloroform/acetic acid (50:40:10) eluent:
Rf of acid: 0.55
Rf of acid chloride: 0.95

XXI. Preparation of 2,4,6-triiodo-5-N-methyl-N-acetylaminobenzoic acid chloride (Compound XXI)

The same procedure is used as for Compound XIX, using 2,4,6-triiodo-3-N-methyl-N-acetylamino-benzoic acid as starting material (Yield: 85%).

XXII. Preparation of 2,4,6-triiodo-3-N-methylcarbamyl-5-N-diacetylamino-benzoic acid chloride (Compound XXII)

a. Diacetylation of 2,4,6-triiodo-3-N-methylcarbamyl-5-aminobenzoic acid (described in U.S. Pat. No. 3,145,197).

800 g of triiodo acid (1.4 mole) are heated overnight at 120° C in 1.6 liter acetic anhydride. The reaction mixture is cooled and an insoluble material (123 g), consisting of starting material, is filtered off. The reaction liquid is slowly poured over water (3 liters) and ice (1 kg). The resulting two phases are decanted. The lower phase is taken up into water (2.4 liters) to give a gum which is redissolved in acetic acid (800 ml). This solution is precipitated by addition of water (5.4 liters) and ice (1 kg). The resulting material is suction filtered and washed repeatedly with water, to give 500 g of wet product which is subsequently used as such.

b. Preparation of the acid chloride

The 500 g of crude product are gradually added to 830 ml thionyl chloride. The temperature decreases. After 30 minutes, 300 ml thionyl chloride are added, followed by 400 ml thionyl chloride 30 minutes later, after which the reaction is completed by heating two hours at 70° C. The thionyl chloride is evaporated in vacuo and the resulting material is taken up into benzene and is then evaporated to dryness, in vacuo. The latter benzene-evaporation treatment is repeated twice, to give 305 g of beige product (overall yield of 38% with respect to the 2,4,6-triiodo-3-N-methylcarbamyl-5-amino-benzoic acid actually used).

Purity control: Same technique as with compound XIX, after condensation with propylamine.

1. TLC: acetone/chloroform/acetic acid (5:4:1) eluent: Rf : 0.83
2. Purity according to iodine titration: 97%
Purity according to titration with sodium methoxide: 101%

XXIII. Preparation of 2,4,6-triiodo-3-N-acetoxyethylcarbamyl-5-N-diacetylamino-benzoic acid chloride (Compound XXIII)

a. Triacetylation of 2,4,6-triiodo-3-N-hydroxyethyl-carbamyl-5-amino-benzoic acid 2,4,6-Triiodo-3-N-hydroxyethylcarbamyl-5-aminobenzoic acid (60.2 g; 0.1 mole) is dissolved in acetic anhydride (150 ml). The solution is heated at 160° C during 48 hours. After cooling, the solution is poured over 250 ml water. The resulting gum is taken up into 3 × 150 ml chloroform. The chloroform is washed with 2 × 100 ml water and dried over calcium chloride; the resulting material is filtered and evaporated in vacuo, to give 60 g of oily product (Yield: 82%).

Purity control:

1. TLC: Eluent 1
Rf of triacetyl — product: 0.75
2. Titration: product is unisolated b. Preparation of the acid chloride 2,4,6-Triiodo-3-N-acetoxyethyl-carbamyl-5-diacetylaminobenzoic acid (60 g; 0.082 mole) is dissolved in thionyl chloride (150 ml). The solution is heated to 80° C during 4 hours. After evaporation in vacuo, the residue is taken up into 100 ml chloroform. A slight insoluble is removed and the acid chloride is precipitated by slowly adding diethyl ether. The resulting material is suction-filtered and dried, to give 45 g of product (i.e., a yield of 73% with respect to the triacetyl product).

Purity control:

1. TLC eluent 1
Rf of acid chloride: 0.9
2. Titration: unisolated.

XXIV. Preparation of 2,4,6-triiodo-3-N-acetoxyethyl-carbamyl-5-N-methyl-N-acetylamino-benzoic acid chloride (Compound XXIV)

a. Acetylation of 2,4,6-triiodo-3-N-hydroxyethyl-carbamyl-5-N-methyl-N-acetylamino-benzoic acid Acetyl chloride (157 g; 2 moles) is added to a suspension of 2,4,6-triiodo-3-N-hydroxyethyl-carbamyl-5-N-methyl-N-acetamidobenzoic acid (658 g; 1 mole) (described in French Pat. No. 2,074,734) in dioxane (2 liters).

The reaction mixture is heated at 80° C during 20 hours. Dissolution occurs. The dioxane is evaporated in vacuo, to give 700 g of acid (i.e., a yield of 100%).

Purity control:

1. TLC eluent 1
Rf of starting material: 0.25
Rr of product obtained: 0.45
2. Purity according to titration: the product is unisolated b. Preparation of the acid chloride The acid obtained above (790 g; 1 mole) is dissolved in thionyl chloride (1200 ml). The reaction mixture is heated at 50° C during two hours. A red solution is obtained. After 48 hours in the refrigerator, the crystalline material is suction-filtered; it is then washed repeatedly with isopropyl ether and dried, to give 485 g of product (Yield: 67%).

Purity control:

1. TLC: eluent 1
Rf of starting material: 0.45
Rf of product obtained: 0.8
2. Purity according to iodine titration: 100%

In following Table IV are set forth the structural formulae of the acid chlorides thus prepared and also those of other know chlorides which are used to prepare the compounds of the general formula I.

TABLE IV

| | |
|---|---|
| 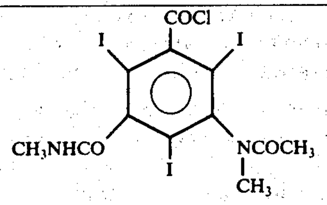 | XIX |
| 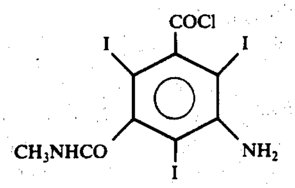 | XX |
| 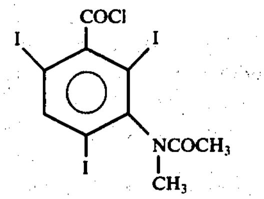 | XXI |
| 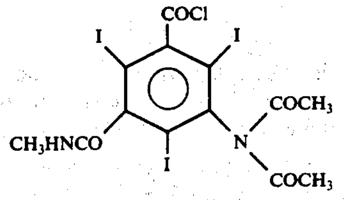 | XXII |
| 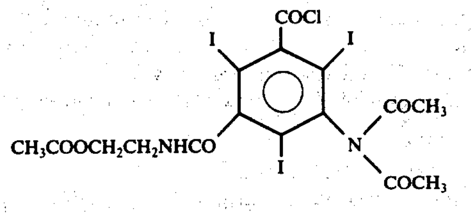 | XXIII |
| 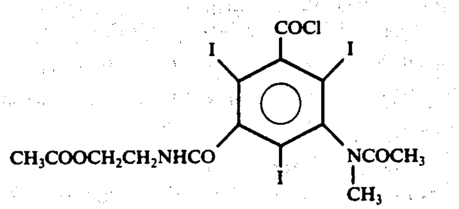 | XXIV |
| 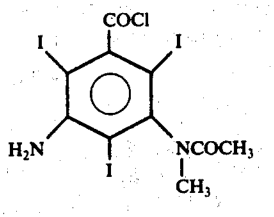 | XXV |
| 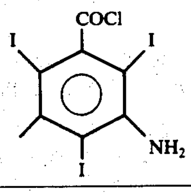 | XXVI |

XXVII. Preparation of 2,4,6-triiodo-3,5-bis-(N-hydroxyethylcarbamyl)-chloracetanilide 2,4,6-Triiodo-3,5-bis-(N-hydroxyethyl-carbamyl)-aniline (645 g; 1 mole) (described in French Pat. No. 1,172,953) is dissolved in 2 liters DMAC (dimethylacetamide), at room temperature. Chloroacetyl chloride (430 ml; 6 moles) is slowly added thereto, while cooling by means of an ice-bath. Stirring is maintained 3 hours at room temperature.

Completion of the reaction is controlled by thin-layer chromatography over Silicagel plate in ethyl acetate/isopropanol/ammonia (55:35:20) eluent. Rf = 0.5. The reaction mixture is poured over water (6 liters), to give a very fine white precipitate which is not readily suction filtered. After washing with water, the resulting 2,4,6-triiodo-3,5-bis-(N-chloroacetoxyethylcarbamyl)-chloroacetanilide is saponified by stirring in 2 liters 2N sodium hydroxide at room temperature during two hours, and then at 40° C during two hours.

Chromatographic control over Silicagel plate, in the same eluent: Rf = 0.35.

The reaction mixture is cooled and neutralized with concentrated hydrochloric acid (100 ml), and stirring is continued overnight at room temperature; after which it is suction filtered, washed with water, suction filtered, dried overnight at 60° C, to give 672 g of product (Yield: 93%).

Purity control:

Titration with sodium methoxide: 105%

Iodine titration: 99%

Chlorine titration: 102.8%

C. PREPARATION OF COMPOUNDS OF THE FORMULA (I)

1) Preparation of 2,4,6-triiodo-3-N-hydroxyethylcarbamyl-5-(2,4,6-triiodo-3-N-methylcarbamyl-5-N-methyl-N-acetylaminobenzoyl)glycylamino-benzoic acid (Compound 1)

a. Condensation 2,4,6-Triiodo-3-N-hydroxyethylcarbamyl-5-aminoacetamidobenzoic acid (Compound I; 165 g; 0.25 mole) is suspended in a mixture of dimethylacetamide (250 ml) and triethylamine (58.50 g). 2,4,6-Triiodo-3-N-methylcarbamyl-5-N-methyl-N-acetylamino-benzoic acid chloride (Compound XIX; 163 g; 0.25 mole) is added to the suspension which is then vigorously stirred at 50° C during 6 hours. TLC is used to control that less than 3% starting materials remain.

The solution is poured over water (1240 ml). The slight precipitate formed is suction filtered. Hydrochloric acid is added to the filtrate to clearly acidic pH. The material is suction filtered, washed with water and dried in an oven at 80° C, to give 186 g of crude product (Yield: 61%).

Purity control:

1. TLC eluent 1:
   Rf of starting amine: 0.05
   Rf of acid chloride: 0.80
   Rf of condensate: 0.15
2. Purity of the product according to titration with sodium hydroxide: 95%
   Purity of the product according to titration with sodium methoxide: 98.5%
   Purity of the product, according to iodine titration: 97%.

b. Purification

Purification is effected by crystallization in the hot, in 95% ethanol.

The product (186 g) is suspended in 95% ethanol (400 ml) and the suspension is then heated to the refluxing temperature. Complete dissolution occurs and, after 6 hours, the product crystallizes. Total heating time is 36 hours. The resulting material is allowed to cool.

After suction-filtering, the wet material is dissolved in an aqueous sodium hydroxide solution (400 ml), after which it is adjusted at pH 4–5 with acetic acid and is then charcoaled twice. The product is then filtered, made acidic to markedly acidic pH with concentrated hydrochloric acid, filtered, washed with water, suction filtered and dried, to give 115 g of pure product (Yield: 62%).

Purity control:

1. TLC: same results as after condensation.
2. Purity: titration with sodium hydroxide: 101%
   Purity: titration with sodium methoxide: 98.5%
   Purity: iodine titration: 100.5%.

2. Preparation of 2,4,6-triiodo-3-N-methylcarbamyl-5-(2,4,6-triiodo-3-N-methylcarbamyl-5-N-methylacetamido-benzoyl)-γ-aminobutyrylamino-benzoic acid (Compound 2)

The same procedure is used as for Compound 1, from amine II and acid chloride XIX.

3. Preparation of 2,4,6-triiodo-3-N-hydroxyethylcarbamyl-5-(2,4,6-triiodo-3-N-methylcarbamyl-5-acetamido-benzoyl)-glycylamino benzoic acid (Compound 3)

This acid is prepared according to two methods:

a. From 2,4,6-triiodo-3-N-hydroxyethylcarbamyl-5-(2,4,6-triiodo-3-N-methylcarbamyl-5-amino-benzoyl)-glycylamino-benzoic acid. (Compound 3*a*). Compound 3*a* is prepared using the same procedure as for Compound 1, from amine I and acid chloride XX. Acetylation of Compound 3*a* gives Compound 3.

b. From 2,4,6-triiodo-3-N-hydroxyethylcarbamyl-5-(2,4,6-triiodo-3-N-methylcarbamyl-5-diacetylamino-benzoyl)-glycylamino-benzoic acid (Compound 3*b*). Compound 3*b* is prepared using the same procedure as for Compound 1, from amine I and acid chloride XXII. Saponification of Compound 3*b* gives Compound 3.

4. Preparation of 2,4,6-triiodo-3-N-methylcarbamyl-5-(2,4,6-triiodo-3-N-hydroxyethylcarbamyl-5-N-acetylamino-benzoyl)-γ-aminobutyrylamino-benzoic acid (Compound 4)

a. 2,4,6-Triiodo-3-N-methylcarbamyl-5-(2,4,6-triiodo-3-N-acetoxyethylcarbamyl-5-N-diacetylamino-benzoyl)-γ-aminobutyrylamino-benzoic acid (Compound 4*a*); obtained using the procedure described for Compound 1, from amine II and acid chloride XXIII.

b. Saponification of Compound 4*a* gives Compound 4.

5. Preparation of 2,4,6-triiodo-3-acetamido-5-(2,4,6-triiodo-3-N-methylcarbamyl-5-N-methylacetamido-benzoyl)-glycylmethylamino-benzoic acid (Compound 5).

The same procedure is used as for Compound 1, from amine IV and acid chloride XIX.

6. Preparation of 2,4,6-triiodo-3-N-hydroxyethylcarbamyl-5-(2,4,6-triiodo-3-acetamido-5-N-methylacetamido-benzoyl)-glycylamino-benzoic acid (Compound 6)

a. 2,4,6-Triiodo-3-N-hydroxyethylcarbamyl-5-(2,4,6-triiodo-3-amino-5-N-methylacetamido-benzoyl)-glycylamino-benzoic acid (Compound 6*a*): Obtained using the procedure described for Compound 1, from amine I and acid chloride XXV.

b. Acetylation of Compound 6*a* gives Compound 6.

7. Preparation of 2,4,6-triiodo-3-N-methylcarbamyl-5-(2,4,6-triiodo-3-N-hydroxyethylcarbamyl-5-N-methylacetamido-benzoyl)-γ-aminobutyrylamino-benzoic acid (Compound 7)

a. 2,4,6-Triiodo-3-N-methylcarbamyl-5-(2,4,6-triiodo-3-N-acetoxyethylcarbamyl-5-N-methylacetamido-benzoyl)-γ-aminobutyrylamino-benzoic acid (Compound 7*a*): obtained using the procedure described for Compound 1, from amine II and acid chloride XXIV.

b. Saponification of Compound 7*a* gives Compound 7.

8. Preparation of 2,4,6-triiodo-3-N-methylcarbamyl-5-(2,4,6-triiodo-3-N-hydroxyethylcarbamyl-5-N-methylacetamido-benzoyl)-glycyl amino-benzoic acid (Compound 8)

a. 2,4,6-Triiodo-3-N-methylcarbamyl-5-(2,4,6-triiodo-3-N-acetoxyethylcarbamyl-5-N-methylacetamido-benzoyl)-glycylamino-benzoic acid (Compound 8*a*): Obtained using the procedure described for Compound 1, from amine III and acid chloride XXIV.

b. Saponification of Compound 8*a* gives Compound 8.

9. Preparation of 2,4,6-triiodo-3-N-methylcarbamyl-5-(2,4,6-triiodo-3-N-methylcarbamyl-5-N-methylacetamido-benzoyl)-glycylamino-benzoic acid (Compound 9)

The procedure described for Compound 1 is used, from amine III and acid chloride XIX.

10. Preparation of 2,4,6-triiodo-5-(2,4,6-triiodo-3-N-methylcarbamyl-5-N-methylacetamido-benzoyl)-γ-aminocaproylamino-benzoic acid (Compound 10)

The procedure described for the preparation of Compound 1 is used, from amine V and acid chloride XIX.

11. Preparation of 2,4,6-triiodo-3-N-methylcarbamyl-5-(2,4,6-triiodo-3-N-methylacetamido-benzoyl)-γ-aminobutyrylamino-benzoic acid (Compound 11)

The procedure described for the preparation of Compound 1 is used, from amine II and acid chloride XXI.

12. Preparation of 2,4,6-triiodo-3-(2,4,6-triiodo-3-acetamidobenzoyl)-glycylamino-benzoic acid (Compound 12)

a. 2,4,6-Triiodo-3-(2,4,6-triiodo-3-amino-benzoyl)-glycylamino-benzoic acid (Compound 12*a*): Obtained using the procedure described for the preparation of Compound 1, from amine VI and acid chloride XXVI.

b. Acetylation of Compound 12*a* gives Compound 12.

13. Preparation of 2,4,6-triiodo-3-(2,4,6-triiodo-3-N-methylacetamido-benzoyl)-glycyl-N-methylamino-benzoic acid (Compound 13)

The procedure described for the preparation of Compound 1 is used, from amine X and acid chloride XXI.

14. Preparation of 2,4,6-triiodo-3-N-methylcarbamyl-5-(2,4,6-triiodo-3-N-methylcarbamyl-5-acetamido-benzoyl)-glycyl-N-methylamino-benzoic acid (Compound 14)

a. 2,4,6-Triiodo-3-N-methylcarbamyl-5-(2,4,6-triiodo-3-N-methylcarbamyl-5-amino-benzoyl)-glycyl-N-methylamino-benzoic acid (Compound 14*a*): Obtained using the procedure described for Compound 1, from amine VIII and acid chloride XX.

b. Acetylation of Compound 14*a* gives Compound 14.

15. Preparation of 2,4,6-triiodo-3-N-methylcarbamyl-5-(2,4,6-triiodo-3-N-methylacetamido-5-amino-benzoyl)-glycylamino-benzoic acid (Compound 15)

The procedure described for Compound 1 is used, from amine III and acid chloride XXV.

16. Preparation of 2,4,6-triiodo-3-N-methylcarbamyl-5-[2,4,6-triiodo-3-N-methylacetamido-5-(2,4,6-triiodo-3-N-methylcarbamyl-5-acetamido-benzoyl)glycylamino-benzoyl]-glycylamino-benzoic acid (Compound 16)

a. 2,4,6-Triiodo-3-N-methylcarbamyl-5-[2,4,6-triiodo-3-N-methylacetamido-5-(2,4,6-triiodo-3-N-methylcarbamyl-5-amino-benzoyl)glycylamino-benzoyl]glycylamino-benzoic acid (Compound 16*a*): Obtained using the procedure described for Compound 1, from amine IX and acid chloride XX.

b. Acetylation of Compound 16*a* gives Compound 16.

17. Preparation of 2,4,6-triiodo-3-N-methylcarbamyl-5-[2,4,6-triiodo-3-N-methylacetamido-5-(2,4,6-triiodo-3-N-methylcarbamyl-5-N-methylacetamido-benzoyl)glycyl-aminobenzoyl]-glycyl-amino-benzoic acid (Compound 17)

The procedure described for Compound 1 is used, from amine IX and acid chloride XIX.

18. Preparation of 2,4,6-triiodo-3-N-methylcarbamyl-5-(2,4,6-triiodo-3-N-methylacetamido-benzoyl-glycyl)-amino-benzoic acid (Compound 18)

The procedure described for Compound 1 is used, from amine III and acid chloride XXI.

19. Preparation of 2,4,6-triiodo-5-(2,4,6-triiodo-3-N-methylcarbamyl-5-N-methylacetamido-benzoyl)glycylamino-benzoic acid (Compound 19)

The procedure described for Compound 1 is used, from amine VI and acid chloride XIX.

20. Preparation of 2,4,6-triiodo-3-acetamido-5-(2,4,6-triiodo-3-N-methylacetamido-5-acetamido-benzoyl)-glycylamino-benzoic acid (Compound 20)

a. 2,4,6-Triiodo-3-acetamido-5-(2,4,6-triiodo-3-N-methylacetamido-5-amino-benzoyl)glycyl-amino-benzoic acid (Compound 20*a*): Obtained as described for Compound 1, from amine VII and acid chloride XXV.

b. Acetylation of Compound 20*a* gives Compound 20.

21. Preparation of 2,4,6-triiodo-3-(2,4,6-triiodo-3-N-methylcarbamyl-5-acetamido-benzoyl)glycyl-N-methylamino-benzoic acid (Compound 21)

a. 2,4,6-Triiodo-3-(2,4,6-triiodo-3-N-methylcarbamyl-5-aminobenzoyl)glycyl-N-methyl amino-benzoic acid (Compound 21*a*): Obtained using the procedure described for Compound 1, from amine X and acid chloride XX.

b. Acetylation of Compound 21*a* gives Compound 21.

22. Preparation of 2,4,6-triiodo-3-(2,4,6-triiodo-3-N-methylcarbamyl-5-N-methylacetamido-benzoyl)-γ-aminobutyrylamino-benzoic acid (Compound 22)

The procedure described for Compound 1 is used, from amine XI and acid chloride XIX.

23. Preparation of 2,4,6-triiodo-3-(2,4,6-triiodo-3-N-methylcarbamyl-5-N-methylacetamido-benzoyl)-β-aminopropionylamino-benzoic acid (Compound 23)

The procedure described for Compound 1 is used, from amine XII and acid chloride XIX.

24. Preparation of acid 2,4,6-triiodo-3-N-hydroxyethylcarbamyl-5-(2,4,6-triiodo-3-N-methylcarbamyl-5-N-methylacetamido-benzoyl)-γ-amino-butyrylamino-benzoic acid (Compound 24)

The procedure described for Compound 1 is used, from amine XIV and acid chloride XIX.

25. Preparation of 2,4,6-triiodo-3-acetamido-5-(2,4,6-triiodo-3-N-methylcarbamyl-5-N-methylacetamido-benzoyl)glycylamino-benzoic acid (Compound 25)

The procedure described for Compound 1 is used, from amine VII and acid chloride XIX.

26. Preparation of 2,4,6-triiodo-3-N-methylacetamido-5-(2,4,6-triiodo-3-N-methylcarbamyl-5-acetamido-benzoyl)-glycylamino-benzoic acid (Compound 26).

a. 2,4,6-Triiodo-3-N-methylacetamido-5-(2,4,6-triiodo-3-N-methylcarbamyl-5-amino-benzoyl)-glycylamino-benzoic acid (Compound 26*a*): Obtained using the procedure described for Compound 1, from amine XIII and acid chloride XX.

b. Acetylation of Compound 26*a* gives Compound 26.

27. Preparation of 2,4,6-triiodo-3-N-methylcarbamyl-5-(2,4,6-triiodo-3-N-methylcarbamyl-5-amino-benzoyl)-glycyl-amino-benzoic acid (Compound 27)

The procedure described for Compound 1 is used, from amine III and acid chloride XX.

28. Preparation of 2,4,6-triiodo-3-N-methylcarbamyl-5-[2,4,6-triiodo-3-N-methylcarbamyl-5-(2,4,6-triiodo-3-N-methylcarbamyl-5-acetamido-benzoyl)-glycylamino-benzoyl]glycyl-N-methylamino-benzoic acid (Compound28)

a. 2,4,6-Triiodo-3-N-methylcarbamyl-5-[2,4,6-triiodo-3-N-methylcarbamyl-5-(2,4,6-triiodo-3-N-methylcarbamyl-5-aminobenzoyl)glycyl-amino-benzoyl]glycyl-N-methylamino-benzoic acid (Compound 28*a*): Obtained using the procedure described for Compound 1, from amine XV and acid chloride XX.

b. Acetylation of Compound 28*a* gives Compound 28.

29. Preparation of 2,4,6-triiodo-3-[2,4,6-triiodo-3-N-methylcarbamyl-5-(2,4,6-triiodo-3-N-methylcarbamyl-5-N-methylacetamido-benzoyl)glycylamino-benzoyl]-glycylamino-benzoic acid (Compound 29)

The procedure described for Compound 1 is used, from amine XVI and acid chloride XIX.

30. Preparation of 2,4,6-triiodo-3-N-hydroxyethylcarbamyl-5-[2,4,6-triiodo-3-N-methylcarbamyl-5-(2,4,6-triiodo-3-N-methylcarbamyl-5-N-methylacetamido-benzoyl)glycylamino-benzoyl]glycylamino-benzoic acid (Compound 30).

The procedure described for Compound 1 is used, from amine XVII and acid chloride XIX.

31. Preparation of 2,4,6-triiodo-3-N-methylcarbamyl-5-bis{[2,4,6-triiodo-3,5-bis(N-hydroxyethylcarbamyl)-phenyl]carbamylmethyl}aminoacetamido-benzoic acid (Compound 31)

A solution of 2,4,6-triiodo-3-N-methylcarbamyl-5-aminoacetamide-benzoic acid (126 g; 0.2 mole) (Compound III) in N sodium hydroxide (220 ml) is mixed with a solution of 2,4,6-triiode-3,5-bis(N-hydroxyethylcarbamyl)-chloroacetanilide (288 g) (XXVII) in N sodium hydroxide (400 ml). Heating is maintained at 85° C during 20 hours, with stirring. The solution is cooled to 20° C and made acidic to pH 1. The resulting gum crystallizes after standing overnight at room temperature. The solid is suction filtered, washed with water and dried, to give 280 g of crude acid. The crude acid is taken up into water, adjusted at pH 7 with ammonia, a slight insoluble is filtered off, and the product is made acidic to pH 1 with dilute (1/10) hydrochloric acid. The precipitate is suction filtered, washed with water and dried, to give 224 g of crude acid.

Titration with sodium hydroxide: 112%.

Purification:

1. Ammonium salt: 224 g of acid are taken up into 150 ml water. Ammonia is added to neutrality. Crystallization occurs. The material is stirred during 24 hours at room temperature. The precipitate is suction filtered, washed with water and taken up into 10N sodium hydroxide until dissolution is complete. This is then precipitated with hydrochloric acid, suction filtered, washed with water and dried, to give 155 g of acid.

Titration with sodium hydroxide: 107%.

2. Methylglucamine salt: a methylglucamine salt solution, containing 28% iodine, is prepared with the 155 g thus obtained. The insoluble is removed by centrifugation and filtration through millipore filter. The filtrate is made acidic to pH1 with hydrochloric acid. The precipitate is suction filtered, and this treatment is repeated once, to give 74 g of acid (overall yield: 18.5%).

Purity of the product is controlled by:

| | |
|---|---|
| TLC, Silicagel plate, n-butanol/water/-acetic acid (50:25:11) | |
| eluent: Rf of starting chloro material | 0.75 |
| Rf of starting amine | 0.25 |
| Rf of condensation product | 0.25 |
| Titration with 0.1N sodium hydroxide | 103% |
| Titration with sodium methoxide | 100% |
| Iodine titration | 97% |

32. Preparation of 2,4,6-triiodo-3-N-methylacetamido-5-bis{[2,4,6-triiodo-3,5-bis(N-Hydroxyethylcarbamyl)-phenyl]-Carbamylmethyl}aminoacetamido-benzoic acid (compound 32)

The procedure described for Compound 31 is used, using amine XIII instead of amine III.

33. Preparation of 2,4,6-triiodo-3-N-methylcarbamyl-5-bis{[2,4,6-Triiodo-3,5-bis(N-hydroxyethylcarbamyl)-phenyl]-carbamylmethyl}amino-N-methylacetamido-benzoic acid (compound 33)

The procedure described for Compound 31 is used, using amine VIII instead of amine III.

34. Preparation of 2,4,6-triiodo-3-(2,4,6-triiodo-3-N-methylcarbamyl-5-aminobenzoyl)glycylamino-benzoic acid Compound 34)

The procedure described for Compound 1 is used, from amine VI and acid chloride XX.

35. Preparation of 2,4,6-triiodo-3-N-methylcarbamyl-5-(2,4,6-triiodo-3-N-methylcarbamyl-5-gluconylamino-benzoyl)-glycylamino-benzoic acid (Compound 35)

a. Condensation:

Using Compound 27 as starting material, a suspension is prepared from Compound 27 (53.5 g; 0.045 mole) and dimethylacetamide (100 ml). Penta-acetyl gluconic acid chloride (39 g; 0.091 mole) (prepared according to C. E. BRAUN & C. D. COOK, Organic Syntheses, Vol. 41, pp 78–82) is added thereto. The reaction mixture is stirred 24 hours at room temperature. It is then poured over 500 ml water. The resulting gum crystallizes after 48 hours in the refrigerator. It is suction filtered and repeatedly washed with water.

TLC in eluent 1:

Rf of starting material: 0.5

Rf of condensation product: 0.35 b. The resulting crude product is dissolved in 300 ml ammonia. It is stirred overnight at room temperature, after which it is evaporated to dryness in vacuo and taken up into 125 ml water. It is then made acidic with dilute (½) hydrochloric acid. After 48 hours in the refrigerator, the precipitate is suction filtered and repeatedly washed with water; it is then dried, to give 35 g of product which is washed with 350 ml ethanol. After suction filtering and drying, the acid is obtained in a yield of 30 g (i.e. an overall yield of 49%).

Purity control:

TLC: eluent 1 : Rf 0.0
eluent 3 : Rf 0.25
eluent 4 : Rf 0.15
Titration with sodium hydroxide: 98%
Iodine titration: 100%

36. Preparation of 2,4,6-triiodo-3-hydroxyethylcarbamyl-5-(2,4,6-triiodo-3-N-methylcarbamyl-5-gluconylamino-benzoyl) glycylamino-benzoic acid (Compound 36)

It is prepared according to the procedure used for Compound 35, from Compound 3*a*.

TLC: eluent 1 : Rf 0.0
eluent 3 : Rf 0.15
eluent 4 : Rf 0.1

37. Preparation of 2,4,6-triiodo-5-(2,4,6-triiodo-3-N-methylacetamido-benzoyl)glycyl-N-methylamino-benzoic acid (Compound 13, 2nd method)

Compound 12 (146 g; 0.13 mole) is dissolved in 4N sodium hydroxide (0.468 mole). Methyl iodide (0.338 mole) is added dropwise thereto, while cooling. After stirring 16 hours at room temperature, the reaction mixture is replenished (in an amount of 10%) with methylating agent and 4N sodium hydroxide. After 48 hours of reaction, the material is precipitated in acidic medium, to give, after repeated suction filtering, washing and then drying, 118.5 g (Yield of the methylation: 72%).

Purity control:

1. TLC eluent 1
Unmethylated product: Rf 0.75
Methylated product: Rf 0.78 and 0.8
2. Eluent 2
Unmethylated product: Rf 0.4
Methylated product: Rf 0.4 and 0.5
3. Eluent 4
Unmethylated product: Rf 0.7
Methylated product: Rf 0.7 and 0.75

Purification: It is effected by salting out the ammonium salt: Yield 80%.
Titration with sodium methoxide: 101%
Titration with sodium hydroxide: 97%

38. Preparation of 2,4,6-triiodo-3-N-methylcarbamyl-5-(2,4,6-triiodo-3-N-methylcarbamyl-5-acetamidobenzoyl)-glycyl-N-methylamino-benzoic acid (Compound 14, 2nd method)

a. Preparation of Compound 14*a* (2nd method):

Compound 27 (11.8 g; 0.01 mole) is dissolved in 2N sodium hydroxide (15 ml; 0.03 mole) and acetone (4 ml). Methyl iodide (2.8 ml; 0.04 mole) is added dropwise thereto. After stirring during 48 hours at room temperature, the reaction mixture is made acidic to pH 1, upon which a precipitate is formed. After repeatedly suction filtering and washing with water, the product is redissolved, adjusted at pH 3–4 and charcoaled. It is then filtered, precipitated, suction filtered and dried, to give 9 g of product (Yield 75%).

Purity control

TLC eluent 1.
Rf of starting material 0.5
Rf of methyl compound 0.6
Titration with sodium methoxide: 98% b. Acetylation of 14*a* to 14 is carried out according to the usual techniques, with $CH_3COCl$ in DMAC solution (Yield 40%).

39. Preparation of 2,4,6-triiodo-3-N-methylcarbamyl-5-(2,4,6-triiodo-3-N-methylcarbamyl-5-N-methylacetamido-benzoyl)-γ-aminobutyryl-N-methylamino-benzoic acid (Compound 37)

Compound 2 (23 g; 0.082 mole) is dissolved in 5N sodium hydroxide (8.3 ml; 0.0418 mole) and water (12 ml). Methyl iodide (5.9 g; 0.0418 mole) is added dropwise thereto. After stirring 24 hours at room temperature, the mixture is made acidic to pH 1. The precipitate is suction filtered, washed with water and dried, to give 20 g of crude acid.

Purification: this is effected by crystallization in the hot from ethanol (20 g/40 ml), under reflux during 3 days. After suction filtering, the product is taken up into alkaline medium and is then charcoaled. After acidic precipitation, the product is suction filtered, washed with water and dried, to give 4.5 g of material (Yield 20%).

Purity control

TLC, eluent 1:
Rf of unmethylated compound: 0.25
Rf of methylated compound: 0.55
TLC, eluent 4:
Rf of unmethylated compound: 0.3 and 0.4
Rf of methylated compound: 0.35; 0.30 & 0.25
Titration with sodium hydroxide: 98%
Titration with sodium methoxide: 98%

40. Preparation of 2,4,6-triiodo-3-N-hydroxyethylcarbamyl-5-(2,4,6-triiodo-3-N-methylcarbamyl-5-acetamido-benzoyl)glycyl-N-methylamino-benzoic acid (Compound 38)

A. Preparation of 2,4,6-triiodo-3-N-hydroxyethylcarbamyl-5-(2,4,6-triiodo-3-N-methylcarbamyl-5-amino-benzoyl)glycyl-N-methylamino-benzoic acid (Compound 38A)

Compound 38*a* is prepared according to the procedure described for Compound 14*a*, from Compound 3*a*, by methylation.

b. Compound 38 is obtained by acetylation of Compound 38*a* according to usual techniques.

41. Preparation of 2,4,6-triiodo-3-N-methylcarbamyl-5-(2,4,6-triiodo-3-N-methylcarbamyl-5-N-methylacetamido-benzoyl)-β-aminopropionylamino-benzoic acid (Compound 39)

Compound 39 is obtained according to the procedure described for Compound 1, from amine XVIII and acid chloride XIX, heating time at 50° C being 3 hours. Crude Yield is 48%.

42. Preparation of 2,4,6-triiodo-3-N-methylcarbamyl-5-(2,4,6-triiodo-3-N-methylcarbamyl-5-N-methylacetamido-benzoyl)-β-aminopropionyl-N-methylamino-benzoic acid (Compound 40)

Compound 40 is obtained by methylation of Compound 39.

In following Table V are set forth data relating to the preparation of compounds of the formula I and to the resulting compounds. The structural formulae of the compounds are given in Table VI.

TABLE V

| Compound | Starting amine | Starting acid chloride | Crude Yield | Rf in eluent 1 | Yield Acetylation + Saponification | Rf in eluent 1 after saponification | Purification Method | Purification Yield | Titration NaOH | Titration MeONa | Titration I | Rf in eluent 1 | Rf in eluent 4 |
|---|---|---|---|---|---|---|---|---|---|---|---|---|---|
| 1 | I | XIX | 61% | 0.15 | | | EtOH | 62% | 100% | 100% | 100% | 0.15 | 0.3 and 0.4 |
| 2 | II | XIX | | 0.25 | | | $NH_4^+$ | 73% | 100% | 98% | 99.5% | 0.25 | 0.3 and 0.4 |
| 3 via 3a | I | XX | 52% 47% (I) | 0.2 | 54% | 0.1 | $NH_4^+$ | 70% | 101% | 99% | 98.5% | 0.1 | 0.1 in eluent 2 |
| 3 via 3b | I | XXII | unisolated | 0.2 | 78% after condensation | 0.1 | $NH_4^+$ | 70% | 101% | 98% | 99% | 0.1 | 0.1 in eluent 2 |
| 4 via 4a | II | XXIII | unisolated | 2.25 | unisolated | 0.15 | EtOH | 17% overall yield | 104% | 97% | 96% | 0.15 | |
| 5 | IV | XIX | 83% | 0.20 | | | $NH_4^+$ | 44% | | 100% | 99% | 0.2 | |
| 6 via 6a | I | XXV | 77% | 0.20 | 76% | 0.12 | $NH_4^+$ | 32% | 102% | 99.3% | 99.8% | 0.12 | 0.15 and 0.2 |
| 7 via 7a | II | XXIV | unisolated | 0.20 | unisolated | 0.1 | $NH_4^+$ | 54% overall yield | 97% | 97% | 99% | 0.10 | |
| 8 via 8a | III | XXIV | unisolated | 0.25 | unisolated | unisolated | $NH_4^+$ | 43% overall yield | 95% | 99% | 98% | 0.25 | 0.3 and 0.35 |
| 9 | III | XIX | 55% | 0.2 | | | Prop OH | 63% | 98.5% | 100% | 99.5% | 0.2 | 0.4 and 0.5 |
| 10 | V | XIX | 68.5% | 0.4 and 0.5 in eluent 4 | | | (4) | 17% | 100% | 96% | 98.5% | 0.4 | 0.4 and 0.5 |
| 11 | II | XXI | 89% | 0.5 | | | $NH_4^+$ | 45% | 100% | 96.5% | 98.5% | 0.5 | 0.25 in eluent 2 |
| 12 via | VI | XXVI | 91% | 0.8 | 81% | 0.75 | unpurified | | | | | 0.75 | |
| 13 | X | XXI | 95% | 0.7 and 0.75 in eluent 4 | | | (4) | | 100% | 100% | 100% | 0.7 | 0.7 and 0.75 |
| 14 via 14a | VIII | XX | 97% | 0.5 | 55% | 0.3 | EtOH | 51% | 100% | 99% | 99% | 0.3 in eluent 2 | 0.35 and 0.4 |
| 15 | III | XXV | 83% | 0.4 | | | unpurified | | | | | 0.40 | |
| 16 via 16a | IX | XX | 84% | 0.3 and 0.4 in eluent 4 | 54% | 0.08 | (5) | 45% | 101% | 99.5% | 98% | | 0.3 and 0.35 |
| 17 | IX | XIX | 68% | 0.15 | | | (5) | 45% | 98% | 100% | 99% | | 0.3 & 0.35 & 0.40 |
| 18 | III | XXI | 86% | 0.35 | | | EtOH twice | 33% | 102% | 101% | 99% | 0.35 | 0.3 in eluent 2 |
| 19 | VI | XIX | 94% | 0.7 in eluent 4 | | | EtOH twice | 41% | 102% | 101% | 98% | 0.52 | 0.7 and 0.45 in eluent 2 |
| 20 via 20a | VII | XXV | 54% (2) | 0.25 and 0.3 | 96% | 0.12 and 0.15 | $NH_4^+$ | 35% | | 103% | 97.5% | | 0.10 in eluent 2 |
| 21 via 21a | X | XX | 80% | 0.7 | 94% | 0.5 | EtOH | 33% | 100% | 102% | 97% | 0.5 | 0.3 in eluent 2 |
| 22 | XI | XIX | 73% | 0.45 | | | EtOH twice | 15% | 99% | 99% | 99% | 0.65 | |
| 23 | XII | XIX | 90% | 0.4 | | | EtOH twice | 66% | 98% | 98% | 99.8% | 0.4 | |
| 24 | XIV | XIX | 79% | 0.15 in eluent 4 | | | EtOH + $NH_4^+$ | 47% | 97% | 97% | 99% | | 0.15 in eluent 4 |
| 25 | VII | XIX | 38% | 0.20 | | | EtOH + $NH_4^+$ | 39% | 90% | 89% | 97% | 0.20 | |
| 26 via 26a | XIII | XX | 69% | 0.40 | 40% | 0.20 glaconylation | $NH_4^+$ | 46% | 98.5% | 98.5% | 99% | 0.20 | |
| 27 | III | XX | 73% | 0.5 | after unisolated | 0.25 | (7) | 49% overall yield | 98% | | 100% | 0.25 | 0.15 |
| 28 via 28a | XV | XX | 97.2% | 0.30 (6) | 83% | 0.15 | EtOH | 16% | 99% | 97.9% | 98% | 0.15 | |
| 29 | XVI | XIX | 87% | 0.35 | | | $NH_4^+$ | 33% | | 104% | 98% | 0.35 | |
| 30 | XVII | XIX | 61% | 0.5 in eluent 2 | | | | | | | | | 0.5 in eluent 2 |
| 31 | III | | 56% | 0.25 in eluent 4 | | | $NH_4^+$ | 33% | 103% | 100% | 97% | | 0.25 |
| 32 | XIII | | 88% | 0.13 | | | EtOH | 45% | 98.5% | 98.5% | 98.5% | 0.13 and | |

TABLE V-continued

| Compound | Starting amine | Starting acid chloride | Crude Yield | Rf in eluent 1 | Yield Acetylation + Saponification | Rf in eluent 1 after saponification | Purification Method | Purification Yield | Titration NaOH | Titration MeONa | Titration I | Rf in eluent 1 | Rf in eluent 4 |
|---|---|---|---|---|---|---|---|---|---|---|---|---|---|
| | | | | and 0.16 (6) | | | twice | | | | | 0.16 (6) | |
| 33 | VIII | | 84% | 0.25 (6) | | | $NH_4^+$ | 38% | 98% | 101% | 100% | 0.25 (6) | 0.55 & 0.6 in eluent 2 |
| 34 | VI | XX | 90% | 0.40 | | | Used crude | | 99.5% | | | 0.40 | |
| 36 | I | XX | 52% | 0.2 | after gluconylation unisolated | 0.25 | (7) | 45% overall yield | 99.7% | 98% | 100% | 0.15 | 0.1 |
| 39 | XVIII | XIX | 48% | | | | | | | | | 0.2 | 0.45 |
| 40 | | | | | | | | | | | | 0.25 and 0.35 | 0.65 |

(1) After one crystallization from 500 ml refluxing ethanol
(2) After one crystallization from ethanol (97 g in 150 ml, under reflux)
(3) After one crystallization from ethanol (405 g/500 ml, under reflux)
(4) Fractional precipitation, with water, of a solution in dimethylformamide
(5) Precipitation, with isopropyl alcohol, of a methanol solution
(6) In eluent: isobutanol/isopropanol/ammonia (60:20:30)
(7) Washing with ethanol.

TABLE VI

1.

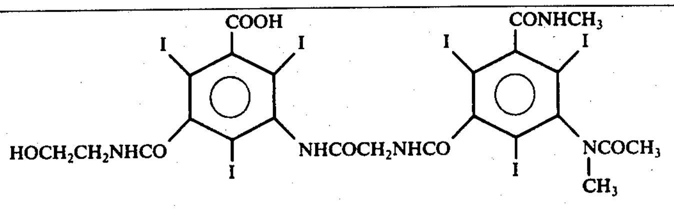

2.

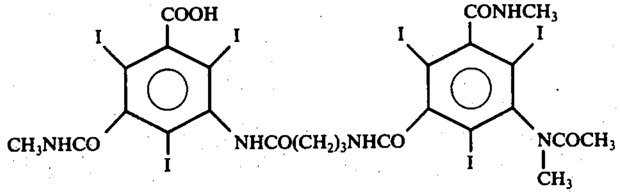

3.

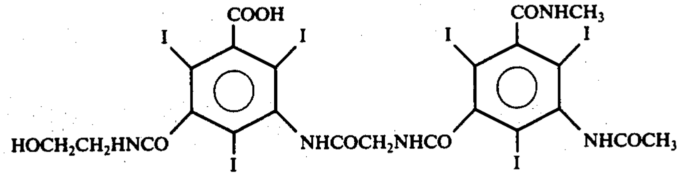

3a.

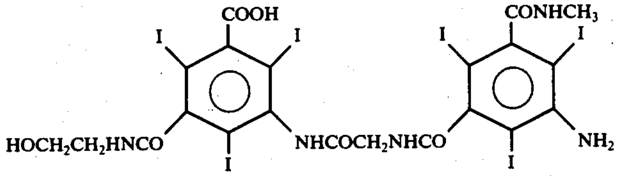

3b.

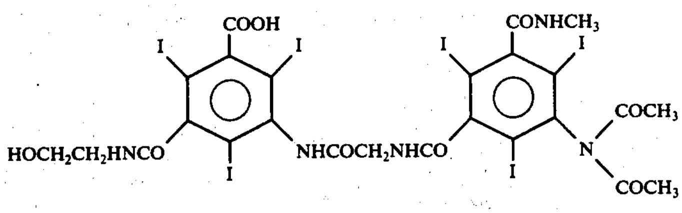

4.

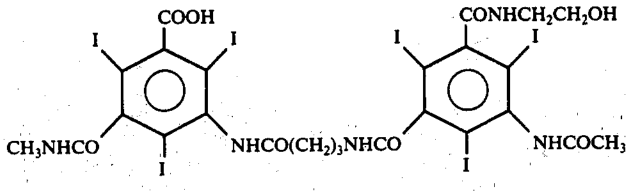

TABLE VI-continued
4a.
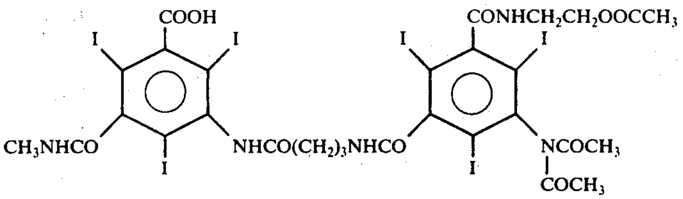
5.
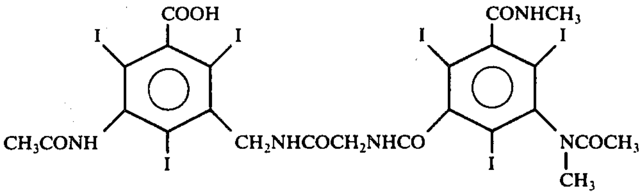
6.
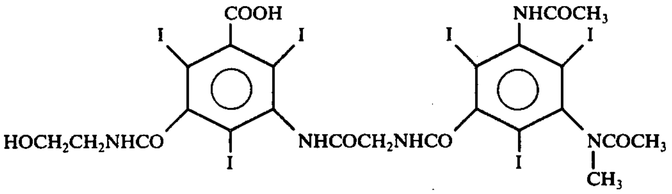
6a.
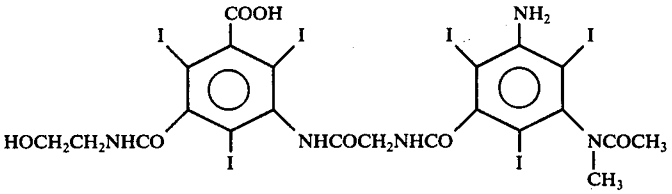
7.
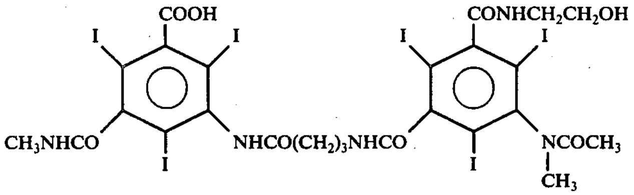
7a.
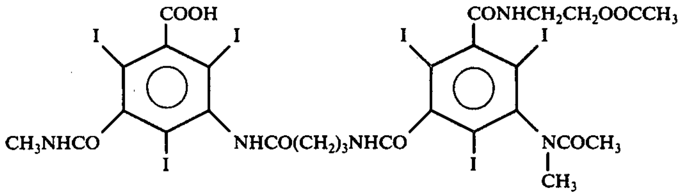
8.
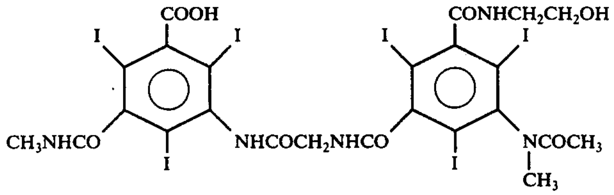
8a.
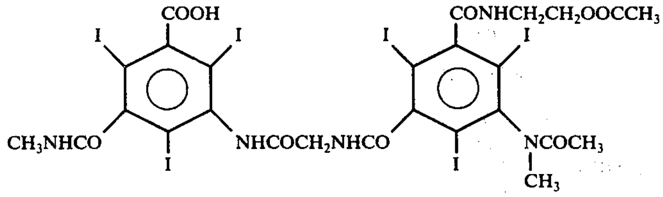

TABLE VI-continued
9.
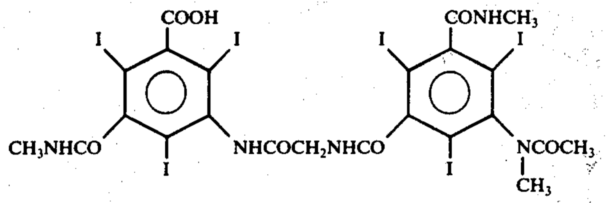
10.
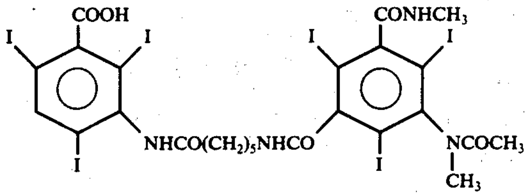
11.
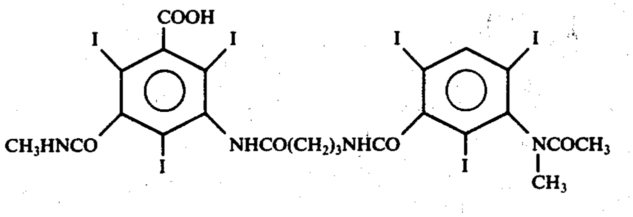
12.
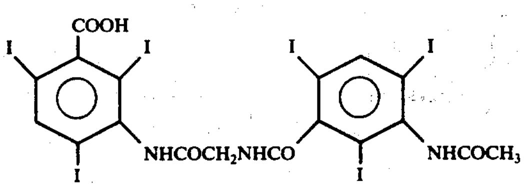
12a.
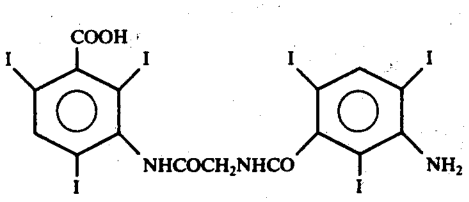
13.
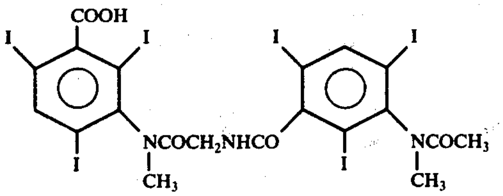
14.
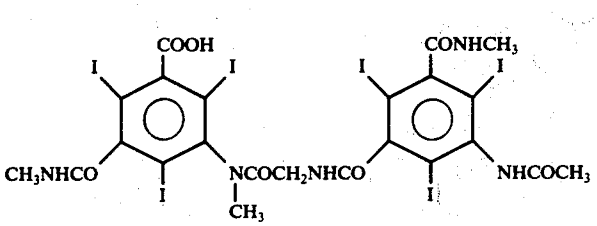
14a.
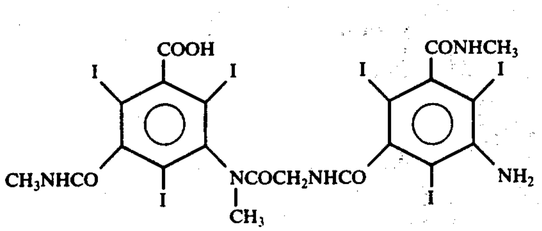

TABLE VI-continued
15.
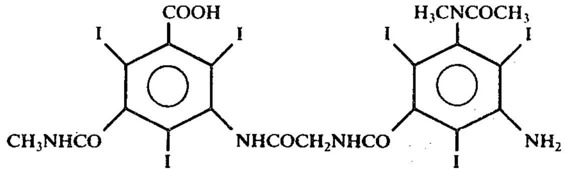
16.
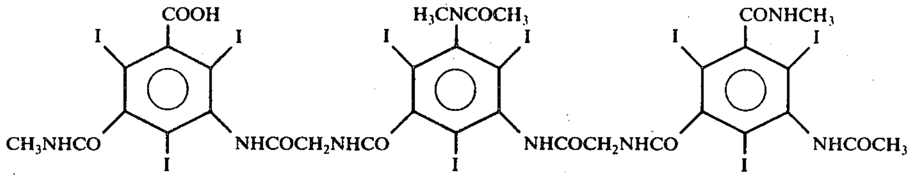
16a.
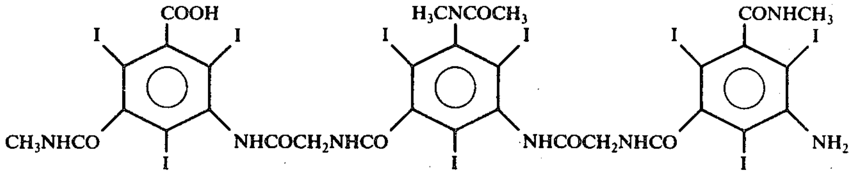
17.
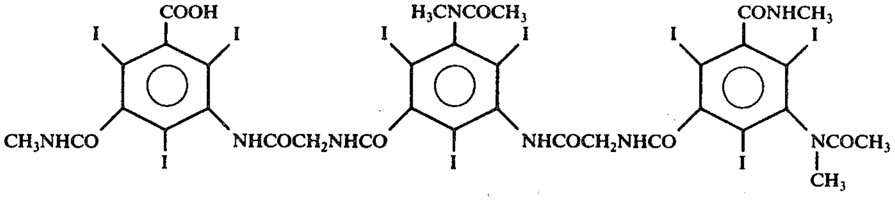
18.
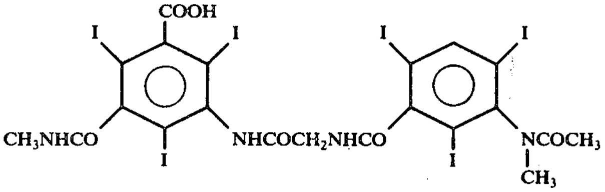
19.
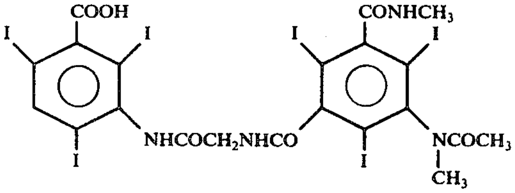
20.
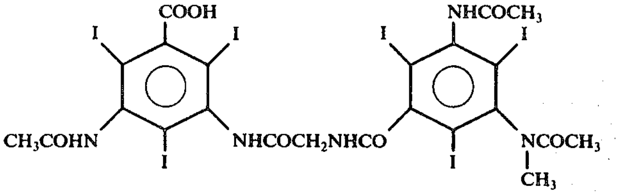
20a.
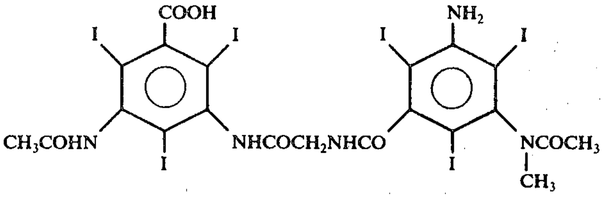

TABLE VI-continued
21.
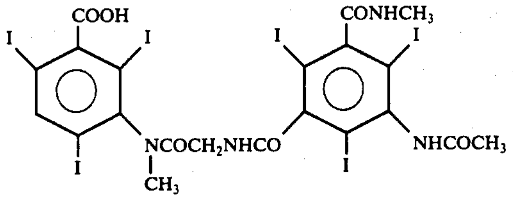
21a.
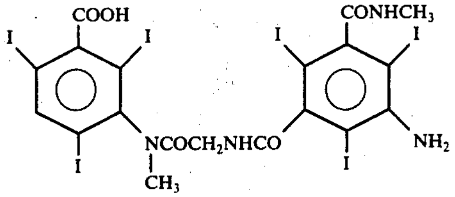
22.
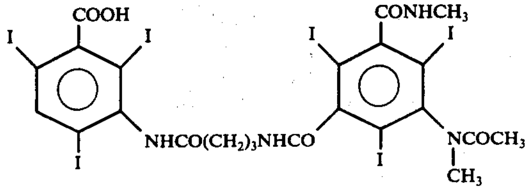
23.
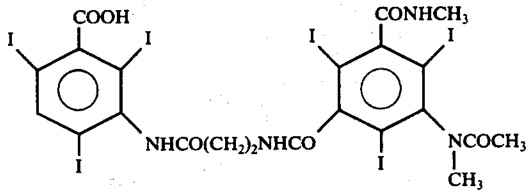
24.
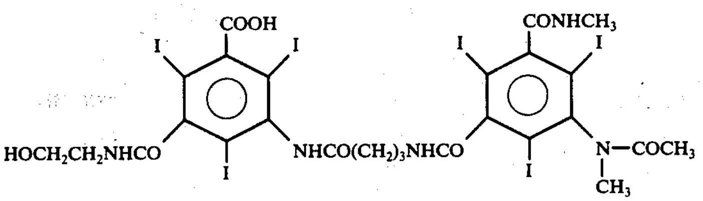
25.
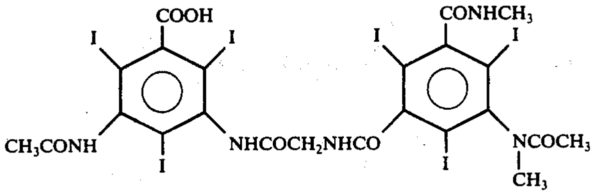
26
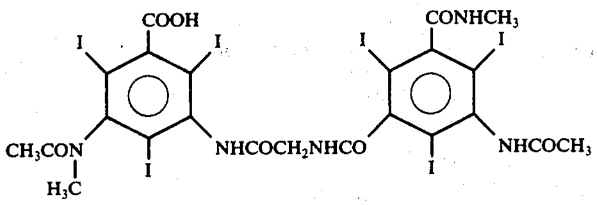
26a.
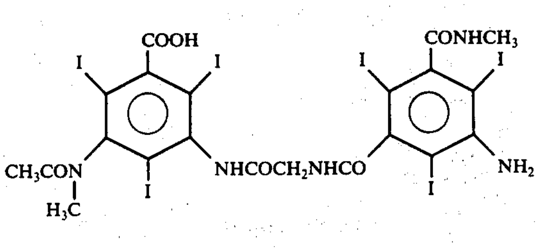

TABLE VI-continued
27.
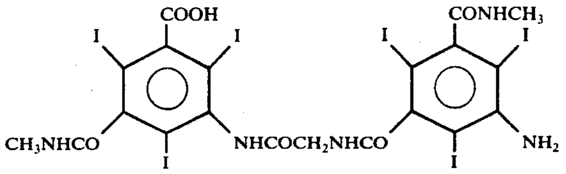
28.
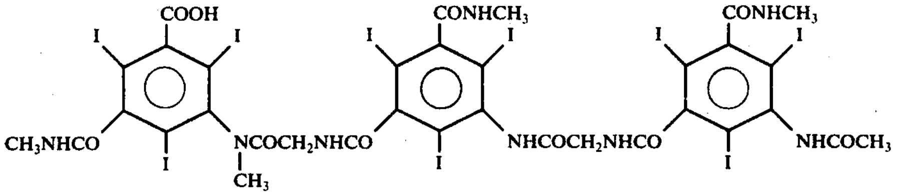
28a.
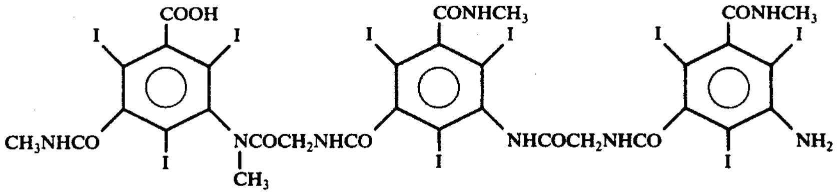
29.
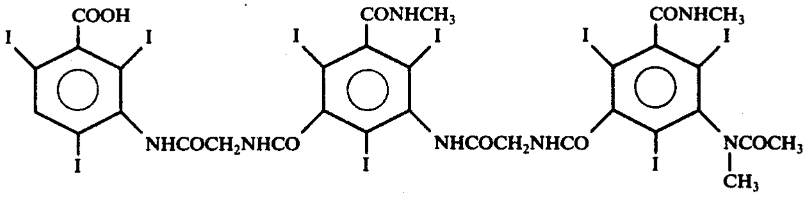
30.
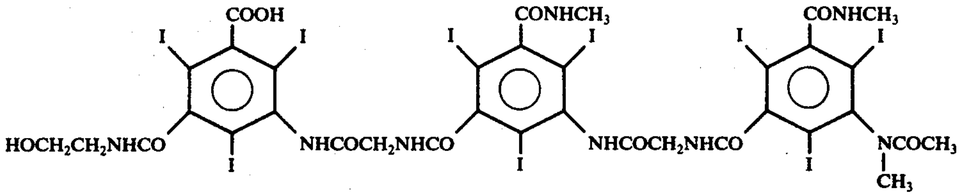
31.
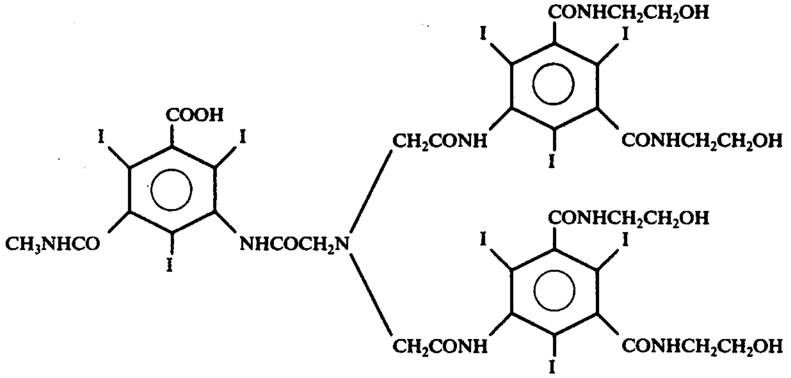
32.
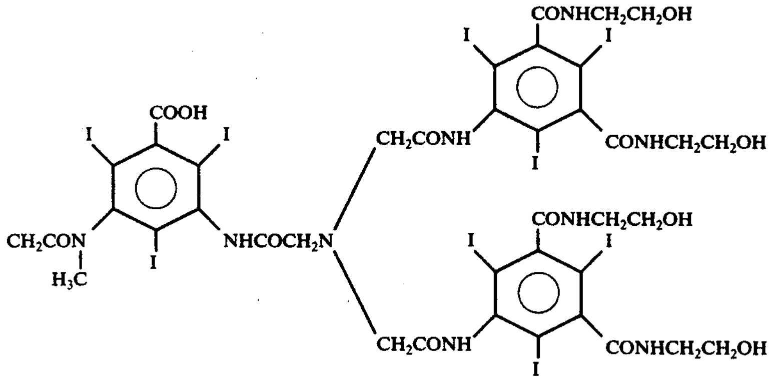

TABLE VI-continued
33.
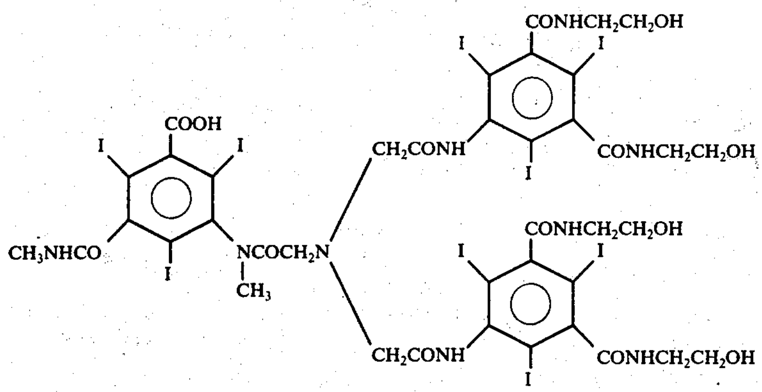
34.
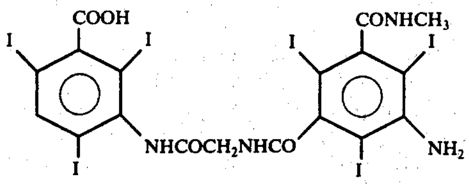
35.
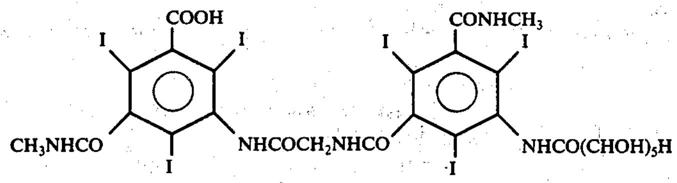
36.
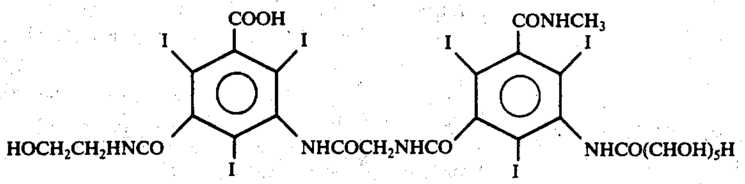
37.
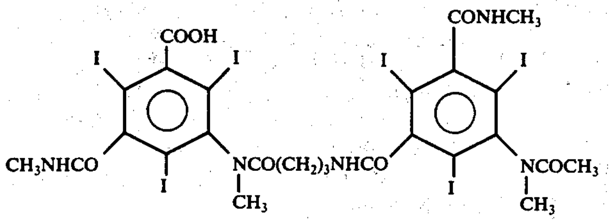
38.
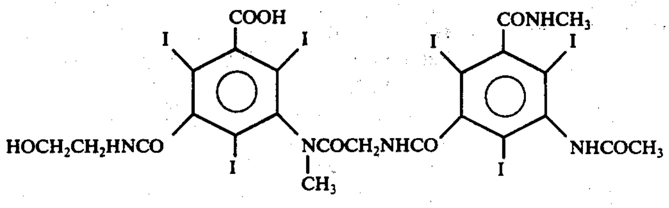
38a.
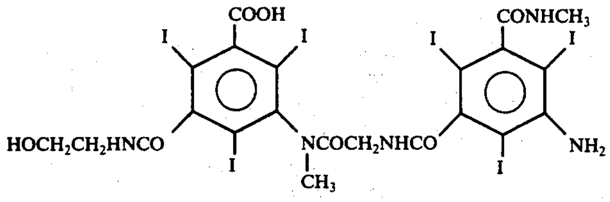
39.
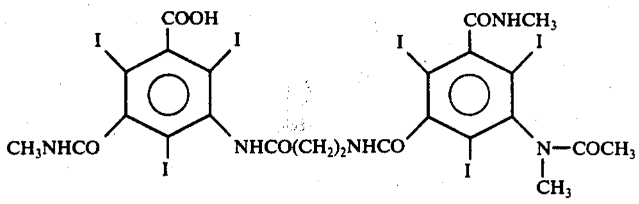

TABLE VI-continued

40.

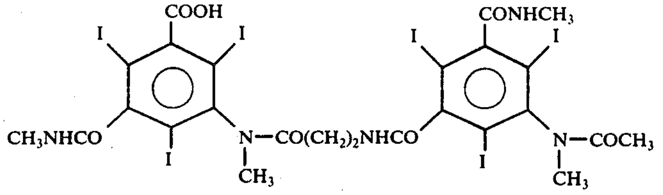

D. Preparation of injectable solutions

Pharmaceutical grade injectable solutions are prepared in the form of the methylglucamine or sodium salt, containing 28, 38 or 48 g iodine per 100 ml (solutions said to contain 28%, 38% and 48% iodine).

After filling the product ino ampoules, under a nitrogen atmosphere, it is sterilized by heating at 120° C during 20 minutes.

The results of viscosity determinations of 28% methylglucamine salt solutions, at 37° C, are given in following Table VII. It is apparent, from said results, that, contrary to expectations, the compounds of the formula (I) have relatively low solution viscosities.

TABLE VII

| Compound | Viscosity, cps. at 37° C |
|---|---|
| | 5.4 |
| 2 | 6.56 |
| 3 | 5.72 |
| 6 | 5.2 |
| 8 | 5.5 |
| 9 | 5.8 |
| 14 | 5.2 |
| 24 | 6 |
| 31 | 10.2 |

The results of osmolality determinations are given in following Table VIII.

Osmolality is determined by extrapolation of the values obtained on successive dilutions of solutions containing 28% or 38% iodine.

Osmolality readings are made with a FISKE Model 230/D/330 D osmometer. This apparatus indicates this measurement as milliosmoles per kg of solution. Its operation is based on the principles of cryoscopy. The determinations were made with solutions containing 28% iodine.

TABLE VIII

| Compound | Osmolality mosm/kg | Compound | Osmolality mosm/kg |
|---|---|---|---|
| 1 | 510 | 17 | 200 |
| 2 | 475 | 18 | 390 |
| 3 | 550 | 19 | 500 |
| 5 | 490 | 20 | 755 |
| 6 | 480 | 37 | 730 |
| 7 | 525 | 21 | 580 |
| 8 | 535 | 23 | 535 |
| 9 | 440 | 38 | 635 |
| 10 | 420 | 24 | 575 |
| 11 | 390 | 25 | 925 |
| 14 | 600 | 26 | 500 |
| 16 | 250 | 31 | 350 |
| | | 32 | 270 |
| | | 33 | 370 |
| a* | 1410 | | |
| b* | 1390 | | |
| c* | 950 | | |

*a, b and c are the following reference compounds:
a: 2,4,6-Triiodo-3-N-methylcarbamyl-5-acetamido-benzoic acid
b: 2,4,6-Triiodo-3-N-hydroxyethylcarbamyl-5-acetamido-benzoic acid
c: 5,5'-Adipoyldiimido-bis-(2,4,6-triiodo-N-methylisophthalamic) acid.

It is apparent that, as the glucamine salts, the compounds of the formula (I) possess an osmolality markedly lower than that of the reference compounds.

The results of a comparative toxicological and pharmacological investigation are given below.

Acute toxicity determination

Intravenous toxicity in mice

Intravenous toxicity determination was effected in Swiss origin, IOPS mice of OFI strain.

Each dosage level was injected to a lot of 10 mice comprising 5 male and 5 female mice.

Injections were made manually, in the caudal vein, at a rate of 2 ml/minute.

Death rate during the 24 hours after injection was recorded.

Biliary clearance test in cats

This test was conducted in male or female adult cats weighing 3-4 kg.

The test material was injected intravenously, at a dosage of 0.10 g/kg iodine at the level of the internal saphenous vein. Clearance of the material was monitored by X-ray control.

X-ray pictures visualizing the gall bladder and the bladder were taken at the following times: 30 minutes, 1 hour, 2 hours, 3 hours, 4 hours, 5 hours, 6 hours.

Effect on the femoral rate of flow

This test was carried out in Nembutal-anesthetized male or female 7-12 kg mongrels.

Nembutal was used at a dosage of 30 mg/kg, with Vetranquil pre-medication, (overall intravenous injection of 2.5 mg), respiration was spontaneous.

Rate of flow variations were recorded at the level of the right or left femoral artery, by means of a Statham electromagnetic sensor.

The injections were made in a collateral of the femoral artery, downstream of the sensor, by means of a catheter mounted by the retrograde route, so as not to perturb the blood flow.

The injections were made under a constant volume of 1.5 ml administered within 3-5 seconds.

The same volume of an isotonic sodium chloride solution was also injected. The resulting data are tabulated in Table IX.

TABLE IX

| Compound No. | I content Nature of the salt | Acute toxicity in mice, i.v.; grams I/kg | Peripheral vasodilatation Femoral rate of flow | Biliary clearance in cat; i.v.; 0.10g I/kg |
|---|---|---|---|---|
| 1 | 38% Mgl | 11.5 | + | ± |
| 2 | 28% Mgl | 9.5 | + | 0 |
| 3 | 28% Mgl | 9-10 | + | |
| 5 | 28% Mgl | 6.8 | ++++ | ± |
| 6 | 28% Mgl | 10 | + | 0 |
| 7 | 28% Mgl | 5 | ++ | 0 |

TABLE IX-continued

| Compound No. | I content Nature of the salt | Acute toxicity in mice, i.v.; grams I/kg | Peripheral vasodilatation Femoral rate of flow | Biliary clearance in cat; i.v.; 0.10g I/kg |
|---|---|---|---|---|
| 8 | 28% Mgl | 12 | ++ | ± |
| 9 | 38% Mgl | 11.5 | + | ++ |
| 10 | 28% Mgl | 1.5 | ++++ | ++++ |
| 11 | 28% Mgl | 2.3 | ++++ | +++ |
| 14 | 28% Mgl | 12 | + | + |
| 16 | 28% Mgl | | + | 0 |
| 17 | 28% Na | | ++ | 0 |
| 18 | 28% Mgl | | ++++ | ++++ |
| 19 | 28% Mgl | 4 | ++++ | ++++ |
| 20 | 28 and 38% Na | 7.5 | + | |
| 21 | 20% Mgl | 4-5 | ++++ | +++ |
| 23 | 28% Mgl | 3.5 | +++ | ++++ |
| 24 | 28% Mgl | 8.5 | + | 0 |
| 25 | 34% Na | 9 | ++ | 0 |
| 26 | 38% Na | 13 | ++ | 0 |
| 31 | 28% Mgl | 15 | + | 0 |
| 32 | 28% Mgl | 15 | + | 0 |
| 33 | 38% Na | 17 | ++ | |
| 35 | 28% Mgl | 8 | + | 0 |
| 36 | 28% Mgl | 8 | ++ | 0 |
| 37 | 28% Mgl | <6 | ++++ | ++ |
| a | 28% Mgl | 5.4 | +++ | 0 |
| b | 30% Mgl | 5.6 | +++ | 0 |
| c | 28% Mgl | 6.2 | ++ | 0 |
| d | 38% mixed Mgl and Na salt | 5.7 | +++ | 0 |
| e | 28% Mgl | 2 | ++++ | ++++ |

a = 2,4,6-Triiodo-3-methylcarbamyl-5-acetamido-benzoic acid
b = 2,4,6-Triiodo-3-N-hydroxyethylcarbamyl-5-acetamido-benzoic acid
c = 5,5'-Adipoyldiimino-bis(2,4,6-triiodo-N-methylisophthalamic) acid
d = 2,4,6-Triiodo-3,5-bis-(acetamido)-benzoic acid
e = 3,3'-Adipoyldiimino-bis(2,4,6-triiodo benzoic) acid
The number of +'s is proportional to the effect observed.

The results of a toxicological investigation effected in rats on intracisternal injection, according to E. Melartin's method (INvestigative Radiology 1970 5, 1, 13-21) are also set forth below.

| Compound | Dosage per rat | Death rate |
|---|---|---|
| 31 | 56 mg I | 1/10 |
| 32 | 50 mg I | 0/10 |
| 33 | 56 mg I | 0/10 |
| c | 17 mg I | 9/10 |

It is apparent from the data reported above that the compounds of the formula (I) are useful as X-ray contrast media. The predominant applications of said compounds are urography, angiography, cholangiography and myelography.

The preferred pharmaceutical form of the X-ray contrast media consists of aqueous solutions of salts of the compounds of the formula (I).

The aqueous solutions contain advantageously 5-100 g of salt per 100 ml and the injectable amount of such solutions may vary within the range from 5 ml to 1,000 ml.

Having now described our invention what we claim as new and desire to secure by Letters Patent is:

1. An iodobenzene derivative selected from the group consisting of a compound of formula

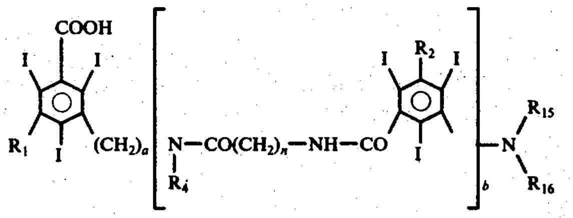

in which:

$R_1$ is selected from the group consisting of a radical having the formula

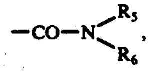

$R_5$ and $R_6$ being each selected from the group consisting of hydrogen, lower alkyl, lower hydroxyalkyl and lower alkanoyloxyalkyl and a radical of the formula

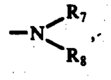

$R_7$ being lower alkanoyl and $R_8$ being selected from the group consisting of hydrogen, lower alkyl and lower hydroxyalkyl, $R_2$ is selected from the group consisting of a radical having the formula

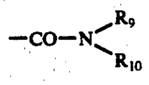

in which $R_9$ and $R_{10}$ have the meanings given for $R_5$ and $R_6$, and a radical of the formula

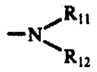

in which $R_{11}$ has the meaning given for $R_7$ or represents hydrogen and $R_{12}$ has the meaning given for $R_8$, at least one of the radicals $R_1$ and $R_2$ being of

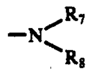 type, $R_4$ is selected from the group consisting of hydrogen, lower alkyl and lower hydroxyalkyl, $R_{15}$ is selected from the group consisting of hydrogen, lower alkanoyl and polyhydroxy lower alkanoyl, $R_{16}$ is selected from the group consisting of hydrogen, lower alkyl, lower hydroxyalkyl and lower alkanoyl,

*a* is 0 or 1

*n* is an integer from 1 to 5

*b* is 1 or 2 and the different $R_2$, $R_4$ and *n* which exist when $b = 2$ may have the same or different meanings, a lower alkyl ester thereof and a salt with a pharmaceutically acceptable base.

2. An X-ray contrast medium comprising an aqueous solution of an effective amount of a compound as claimed in claim 1.

3. An X-ray contrast medium comprising an aqueous solution of an effective amount of a pharmaceutically acceptable salt of a compound as claimed in claim 1.

4. An X-ray contrast medium as claimed in claim 3 in which 100 ml of said solution contains 5-100 g of said salt.

* * * * *